United States Patent
Bennani et al.

(10) Patent No.: US 7,932,245 B2
(45) Date of Patent: Apr. 26, 2011

(54) SPIROCYCLOPROPYL AMIDES AND ACIDS AND THEIR THERAPEUTIC APPLICATIONS

(75) Inventors: Youssef L. Bennani, Shaker Heights, OH (US); William H. Bunnelle, Mundelein, IL (US); Sou-Jen Chang, Prairie View, IL (US); Sanjay R. Chemburkar, Gurnee, IL (US); Jinhua Chen, Gurnee, IL (US); Michael J. Dart, Highland Park, IL (US); Dilinie P. Fernando, Gurnee, IL (US); Yi-Yin Ku, Buffalo Grove, IL (US); Mark Lockwood, Alpharetta, GA (US); Lei Wang, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 629 days.

(21) Appl. No.: 10/691,095

(22) Filed: Oct. 22, 2003

(65) Prior Publication Data
US 2004/0204396 A1 Oct. 14, 2004

Related U.S. Application Data

(60) Provisional application No. 60/420,286, filed on Oct. 22, 2002.

(51) Int. Cl.
*A61K 31/397* (2006.01)
*A61K 31/535* (2006.01)
*A61K 31/4965* (2006.01)
*A61K 31/445* (2006.01)

(52) U.S. Cl. ............ 514/210.01; 514/237.5; 514/227.2; 514/255.01; 514/317; 514/423

(58) Field of Classification Search .................. 514/210, 514/237.5, 227.2, 255.01, 317, 423
See application file for complete search history.

(56) References Cited

FOREIGN PATENT DOCUMENTS
CA 2407777 11/2001

OTHER PUBLICATIONS

Remington's Pharmaceutical Sciences, Mack Publishing Co. 15th Edition, 1975, pp. 411-415.*
Concellon et al., Complete Stereospecific Cyclopropanation of α,β-Unsaturated Amides Promoted by Sm/CH2I2, Angewandte Chemie Int. Ed. 2002, 41, No. 11 pp. 1917-1919, Jun. 3, 2002.*
De Kimpe et al., Straightforward Synthesis of 1-Amino-2,2-dialkylcyclopropanecarboxylic Acids via Selective Saponification of 2,2-Dialkylcyclopropane-1,1-dicarboxylic Esters and Curtius Rearrangement, J. Org. Chem. 1994,vol. 59, pp. 8215-8219.*
Arbale et al, "Synthesis of ethy/isopropyl/3-phenoxybenzyl/α-cyano-3-phenoxybenzyl(±)-cis-and(±)-trans-2-alkyl/aryl-4-oxo/hydroxy/acetoxy-spiro[2,5]octane and spiro[2,4]heptane-1-caboxylates," Indian Journal of Chemistry, 29B, 568-571, (1990).

* cited by examiner

*Primary Examiner* — Yvonne L Eyler
*Assistant Examiner* — Donna Jagoe
(74) *Attorney, Agent, or Firm* — Andreas Danckers; Paul Yasger

(57) ABSTRACT

The present invention relates to the use of compounds of formula (I)

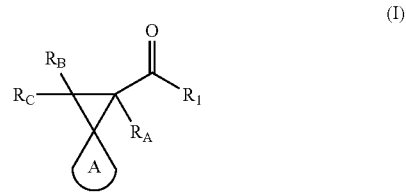

for the treatment of epilepsy, bipolar disorder, psychiatric disorders, migraine, pain, or movement disorders, and to provide neuroprotection.

11 Claims, No Drawings

SPIROCYCLOPROPYL AMIDES AND ACIDS AND THEIR THERAPEUTIC APPLICATIONS

This application claims priority to U.S. Provisional Application Ser. No. 60/420,286, filed Oct. 22, 2002.

TECHNICAL FIELD

The present invention relates to spirocyclopropyl amides and acids, to the use of these compounds to treat epilepsy, bipolar disorder, psychiatric disorders, migraine, pain, movement disorders, and to the use of these compounds to provide neuroprotection, and to the preparation of these compounds.

BACKGROUND OF THE INVENTION

Epilepsy is a common neurological disorder characterized by spontaneous recurrent seizures resulting from abnormal electrical discharges in the brain. It is a health problem that affects roughly 1% of the worldwide population (Loscher, W., Current status and future directions in the pharmacotherapy of epilepsy, Trends Pharmacol. Sci., 2002, 23 (3), 113-118). Epileptic seizures are divided into two major groups, partial or generalized. Partial (focal or local) seizures originate from one or more localized parts of the brain, whereas generalized seizures simultaneously emanate from both brain hemispheres. More than 40 distinct epilepsies have been identified and are characterized by a variety of factors including type of seizure, etiology, age of onset, severity, and EEG features (Commission on Classification and Terminology of the International League Against Epilepsy, Proposal for revised classification of epilepsies and epileptic syndromes, Epilepsia, 1989, 30 (4), 389-399). Epileptic disorders encompass a broad range of severities, extending from a mild and benign condition that readily responds to antiepileptic or anticonvulsant drug (AED) treatment, to a severe, debilitating and even life-threatening condition in which the recurrent seizures remain intractable to drug treatment.

Numerous drugs are now available for the symptomatic treatment of epilepsy. Among these are "first generation" AEDs such as phenytoin, carbamazepine, phenobarbital, and valproate. Several new AEDs or "second generation" drugs such as lamotrigine, topiramate, vigabatrin, felbamate, oxcarbazepine, tiagabine, gabapentin, zonisamide, and levetiracetam have entered the marketplace in the last 15 years (Perucca, E., Clinical pharmacology and therapeutic use of the new antiepileptic drugs, Fundamental & Clinical Pharmacology, 2001, 15, 405-417). Although the newer AEDs provide benefits, significant efficacy and safety issues remain (Schmidt, D., The clinical impact of new antiepileptic drugs after a decade of use in epilepsy, Epilepsy Res., 2002, 50(1-2), 21-32; Asconape, J. J., Some common issues in the use of antiepileptic drugs, Seminars in Neurology, 2002, 22(1), 27-39; and Wallace, S. J., Newer antiepileptic drugs: advantages and disadvantages, Brain & Development, 2001, 23, 277-283). For example, roughly one third of epileptic patients continue to have seizures. (Loscher, W. and Schmidt, D., New horizons in the development of antiepileptic drugs, Epilepsy Res., 2002 50 (1-2), 3-16). Thus, an urgent and unmet need exists for new AEDs with improved safety and efficacy.

The mechanisms of action of many AEDs are not well characterized, and for some, completely unknown. However, AEDs manage to strike a balance between inhibitory and excitatory mechanisms within the CNS, which ultimately can prevent seizures. At the cellular level, this antiseizure effect appears to be produced by several mechanisms that are generally divided into three main categories: modulation of voltage-gated ion channels (sodium, calcium, and potassium), indirect or direct enhancement of γ-aminobutyric acid (GABA)-mediated inhibitory neurotransmission, and inhibition of excitatory (particularly glutamate-mediated) neurotransmission (Kwan, P., Sills, G., Brodie, M. J., The mechanisms of action of commonly used antiepileptic drugs, Pharmacology & Therapeutics, 2001, 90, 21-34; Soderpalm, B., Anticonvulsants: aspects of their mechanisms of action, Eur. J. Pain, 2002, 6(Suppl A), 3-9). Many AEDs exert their actions through multiple mechanisms. In addition, numerous other less well-characterized mechanisms might also be operative and contribute to the biological activity of these drugs.

Several drugs developed initially as AEDs exhibit beneficial effects in a number of common neurological and psychiatric disorders including bipolar disorders, migraine, neuropathic pain, and movement disorders (Beghi, E., The use of anticonvulsants in neurological conditions other than epilepsy, CNS Drugs, 1999, 11 (1), 61-82). The spectrum of uses for AEDs in psychiatric disorders continues to expand. It has been reported that one third of patients currently taking AEDs do so for the treatment of diverse CNS disorders other than epilepsy (Lopes da Silva, F., Post, R. M., Evaluation and prediction of effects of antiepileptic drugs in a variety of other CNS disorders, Epilepsy Research, 2002, 50(1-2), 191-193). Given the increasingly diverse range of clinical utility being recognized with AEDs, it is likely that new chemical entities, which display broad-spectrum anticonvulsant activity, may also show beneficial effects for the treatment of a variety of neurological and psychiatric disorders.

Several AEDs are used clinically to treat the various aspects of bipolar disorder, which is a chronic, cyclic disease characterized by disruptive mood swings from mania to depression. It is a chronic disorder that affects more than 1% of the US population. Carbamazepine was the first AED utilized to treat bipolar disorder (Brambilla, P., Barale, F., Soares, J. C., Perspectives on the use of anticonvulsants in the treatment of bipolar disorder, International Journal of Neuropsychopharmacology, 2001, 4, 421-446). Valproate has more recently emerged and now competes with lithium as a first-line treatment for patients with bipolar disorder, in particular the manic episodes associated with this illness (Angel, I. and Horovitz, T., Bipolar disorder and valproic acid, Current Opinion in Central & Peripheral Nervous System Investigational Drugs (1999), 1(4), 466-469; Bowden, C. L., Brugger, A. M., Swann, A. C., Calabrese, J. R., Janicak, P. G., Petty, F., Dilsaver, S. C., Davis, J. M., Rush, A. J., Small, J. G., Garza-Trevino, E. S., Risch S. C., Goodnick, P. J., Morris, D. D., Efficacy of divalproex vs lithium and placebo in the treatment of mania. The Depakote Mania Study Group, JAMA, 1994, 271(12), 918-24). Lamotrigine has shown beneficial effects in the treatment of bipolar depression (Muzina, D. J., El-Sayegh, S., Calabrese, J. R., Antiepileptic drugs in psychiatry-focus on randomized controlled trial, Epilepsy Research, 2002, 50 (1-2), 195-202; Calabrese, J. R., Shelton, M. D., Rapport, D. J., Kimmel, S. E., Bipolar disorders and the effectiveness of novel anticonvulsants, J. Clin. Psychiatry, 2002, 63 (suppl 3), 5-9).

In addition to bipolar disorder, a number of neuropsychiatric syndromes and disorders may be treated with AEDs (Bialer, M., Johannessen, S. I., Kupferberg, H. J., Levy, R. H., Loiseau, P., Perucca, E., Progress report on new antiepileptic drugs: a summary of the sixth eilat conference (EILAT VI), Epilepsy Res. 2002, 51, 31-71; Fountain, N. B., Dreifuss, F. E., The future of valproate. In: Valproate., Loscher W., Editor. 1999, Birkhauser Verlag, Boston). Such psychiatric disorders include: anxiety and panic disorders, post-traumatic stress disorder, schizophrenia, episodic dyscontrol, substance-abuse-related disorders, impulse control disorders, general agitation associated with a variety of psychiatric disorders and dementias, and behavioral disorders associated with autism.

Migraine is defined as a periodically occurring vascular headache characterized by pain in the head (usually unilateral), nausea and vomiting, photophobia, phonophobia, vertigo and general weakness. It is associated with episodic as well as long-term disability and suffering. Migraine is the most common type of vascular headache and affects as much as 15% of the world's population (Krymchantowski, A. V., Bigal, M. E., Moreira, P. E., New and emerging prophylactic agents for migraine, CNS Drugs, 2002, 16 (9), 611-634). Several AEDs have been shown to be effective in the prevention of migraine including valproate, lamotrigine, gabapentin, and topiramate (Wheeler, S. D., Antiepileptic drug therapy in migraine headache, Current Treatment Options in Neurology, 2002, 4, 383-394; Krymchantowski, A. V., Bigal, M. E., Moreira, P. E., New and emerging prophylactic agents for migraine, CNS Drugs, 2002, 16 (9), 611-634). Many AEDs act by attenuating cellular hyperexcitability and providing a balance between GABAergic inhibition and excitatory amino acid-mediated neuronal excitation, factors that may play a role in the pathophysiology of migraines.

Pain is a common symptom of disease and a frequent complaint with which patients present to physicians. Pain is commonly segmented by duration (acute vs. chronic), intensity (mild, moderate, and severe), and type of pain (nociceptive vs. neuropthic). Neuropathic pain encompasses a wide range of pain syndromes of diverse etiologies and is characterized by a neuronal hyperexcitablility in damaged areas of the nervous system. Diabetic neuropathy, cancer neuropathy, and HIV pain are the most commonly diagnosed types of neuropathic pain. Neuropathic pain also afflicts a significant number of patients suffering from a wide range of other disorders such as trigeminal neuralgia, post-herpetic neuralgia, traumatic neuralgia, phantom limb, as well as numerous other painful disorders of ill-defined or unknown origin. Patients generally respond poorly to traditional pain therapeutic approaches and new drugs with improved efficacy, tolerability, and safety are needed.

Carbamazepine was the first AED examined in controlled trials for neuropathic pain and the results support its use in the treatment of paroxysmal attacks in trigeminal neuralgia, post-herpetic neuralgia, and diabetic neuropathy (Jensen, T. S., Anticonvulsants in neuropathic pain: rationale and clinical evidence, Eur. J. Pain, 2002, 6 (suppl A), 61-68). Among the AEDs examined in controlled trials, gabapentin has clearly demonstrated analgesic effects in treating postherpetic neuralgia and painful diabetic neuropathy (Tremont-Lukats, I. W., Megeff, C., Backonja, M.-M., Anticonvulsants for neuropathic pain syndromes: mechanisms of action and place in therapy, Drugs, 60 (5), 1029-1052). Lamotrigine has demonstrated efficacy in relieving pain in patients with trigeminal neuralgia refractory to other treatments (Backonja, M.-M., Anticonvulsants (antineuropathics) for neuropathic pain syndromes, Clin. J. Pain, 2000, 16, S67-S72). Pregabalin, a follow-on compound to gabapentin, has shown efficacy in clinical trials for diabetic neuropthy. In addition, numerous AEDs display antinociceptive, antiallodynic, or antihyperalgesic activity in animal models relevant to a variety of pain states. Therefore, the potential exists for new AEDs to benefit patients suffering from pain.

AEDs have also been used clinically to treat a variety of movement disorders (Magnus, L., Nonepileptic uses of gabapentin, Epilepsia, 1999, 40 (suppl 6), S66-S72; Fountain, N. B., Dreifuss, F. E., The future of valproate. In: Valproate., Löscher W., Editor. 1999, Birkhauser Verlag, Boston; Cutter, N., Scott, D. D., Johnson, J. C., Whiteneck, G., Gabapentin effect on spacticity in multiple sclerosis, a placebo-controlled, randomized trial, 2000, 81, 164-169), and shown positive effects in animal models of movement disorders (Löscher W., Richter, A., Piracetam and levetiracetam, two pyrrolidone derivatives, exert antidystonic activity in a hamster model of paroxysmal dystonia, Eur. J. Pharmacol., 2000, 391, 251-254). Movement disorders include restless leg syndrome, essential tremor, acquired nystagmus, post-anoxic myoclonus, spinal myoclonus, spasticity, chorea, and dystonia.

Many AEDs have demonstrated some evidence of neuroprotective activity in a variety of ischemia models (Pitkanen, A., Efficacy of current antiepileptics to prevent neurodegeneration in epilepsy models, Epilepsy Research, 2002, 50, 141-160). These neuroprotective effects indicate that AEDs could be useful in the treatment of stroke, in mitigating brain damage after recovery from cardiac arrest, and in preventing epileptogenesis.

The present invention relates to compounds that are anticonvulsants and therefore can be used to treat a variety of indications including, but not limited to, epilepsy, bipolar disorder, psychiatric disorders, migraine, pain, movement disorders, and to provide neuroprotection.

SUMMARY OF THE INVENTION

In its principle embodiment, the present invention relates to a method of treating migraine, epilepsy, or bipolar disorder in a mammal, particularly in a human, comprising administering to a mammal a therapeutically effective amount of a compound of formula (I)

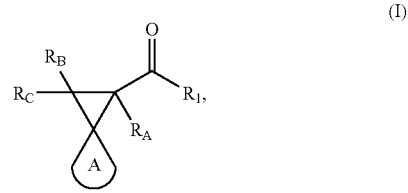

or a pharmaceutically acceptable prodrug thereof, wherein
A is cycloalkyl or bicycloalkyl;
$R_A$, $R_B$, and $R_C$ are independently hydrogen or alkyl;
$R_1$ is $OR_2$ or $NR_3R_4$;
$R_2$ is hydrogen, alkyl, aryl, arylalkyl, cycloalkyl, cycloalkylalkyl, heterocycle, or heterocyclealkyl;
$R_3$ and $R_4$ are independently hydrogen, alkenyl, alkyl, alkynyl, alkoxycarbonylalkyl, aryl, arylalkyl, carboxyalkyl, cycloalkyl, cycloalkylalkyl, heterocycle, heterocyclealkyl, hydroxyalkyl, $(NR_5R_6)$alkyl, $(NR_5R_6)$carbonylalkyl, or

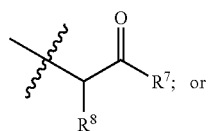

$R_3$ and $R_4$ taken together with the nitrogen atom to which they are attached form a heterocycle wherein the heterocycle is azepanyl, azetidinyl, aziridinyl, morpholinyl, piperazinyl, piperidinyl, pyrrolidinyl, or thiomorpholinyl;

$R_5$ and $R_6$ are independently hydrogen, alkenyl, alkyl, alkynyl, alkoxycarbonylalkyl, aryl, arylalkyl, cycloalkyl, cycloalkylalkyl, heterocycle, heterocyclealkyl, or hydroxyalkyl;

$R_7$ is alkoxy, alkyl, hydroxy, or —$NR_5R_6$;

$R_8$ is alkenyl, alkoxyalkyl, alkoxycarbonylalkyl, alkylthioalkyl, alkynyl, aryl, arylalkyl, carboxyalkyl, cycloalkyl, cycloalkylalkyl, heterocycle, heterocyclealkyl, hydroxyalkyl, mercaptoalkyl, ($NR_5R_6$)alkyl, ($NR_5R_6$)carbonylalkyl, or —$(CH_2)_n NHC(=NH)NH_2$; and n is an integer from 1 to 6.

DETAILED DESCRIPTION OF THE INVENTION

All patents, patent applications, and literature references cited in the specification are herein incorporated by reference in their entirety.

In its principle embodiment, the present invention relates to a method of treating migraine, epilepsy, or bipolar disorder in a mammal, particularly in a human, comprising administering to a mammal a therapeutically effective amount of a compound of formula (I)

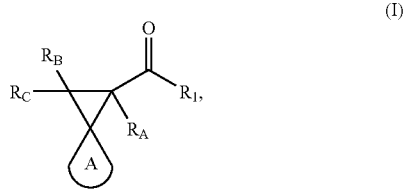

(I)

or a pharmaceutically acceptable prodrug thereof, wherein

A is cycloalkyl or bicycloalkyl;

$R_A$, $R_B$, and $R_C$ are independently hydrogen or alkyl;

$R_1$ is $OR_2$ or $NR_3R_4$;

$R_2$ is hydrogen, alkyl, aryl, arylalkyl, cycloalkyl, cycloalkylalkyl, heterocycle, or heterocyclealkyl;

$R_3$ and $R_4$ are independently hydrogen, alkenyl, alkyl, alkynyl, alkoxycarbonylalkyl, aryl, arylalkyl, carboxyalkyl, cycloalkyl, cycloalkylalkyl, heterocycle, heterocyclealkyl, hydroxyalkyl, ($NR_5R_6$)alkyl, ($NR_5R_6$)carbonylalkyl, or

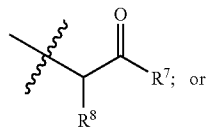

$R_3$ and $R_4$ taken together with the nitrogen atom to which they are attached form a heterocycle wherein the heterocycle is azepanyl, azetidinyl, aziridinyl, morpholinyl, piperazinyl, piperidinyl, pyrrolidinyl, or thiomorpholinyl;

$R_5$ and $R_6$ are independently hydrogen, alkenyl, alkyl, alkynyl, alkoxycarbonylalkyl, aryl, arylalkyl, cycloalkyl, cycloalkylalkyl, heterocycle, heterocyclealkyl, or hydroxyalkyl;

$R_7$ is alkoxy, alkyl, hydroxy, or —$NR_5R_6$;

$R_8$ is alkenyl, alkoxyalkyl, alkoxycarbonylalkyl, alkylthioalkyl, alkynyl, aryl, arylalkyl, carboxyalkyl, cycloalkyl, cycloalkylalkyl, heterocycle, heterocyclealkyl, hydroxyalkyl, mercaptoalkyl, ($NR_5R_6$)alkyl, ($NR_5R_6$)carbonylalkyl, or —$(CH_2)_n NHC(=NH)NH_2$; and n is an integer from 1 to 6.

In another embodiment, the present invention relates to a method of treating epilepsy, migraine, or bipolar disorder in a mammal comprising administering to a mammal a therapeutically effective amount of a compound of formula (I) wherein A is cycloalkyl; $R_1$ is $OR_2$; and $R_A$, $R_B$, $R_C$, and $R_2$ are as defined in formula (I).

In another embodiment, the present invention relates to a method of treating epilepsy, migraine, or bipolar disorder in a mammal comprising administering to a mammal a therapeutically effective amount of a compound of formula (I) wherein A is cycloalkyl wherein the cycloalkyl is cyclohexyl optionally substituted with 1, 2, 3, or 4 alkyl groups; $R_1$ is $OR_2$; $R_2$ is hydrogen; and $R_A$, $R_B$, and $R_C$ are as defined in formula (I).

In another embodiment, the present invention relates to a method of treating epilepsy, migraine, or bipolar disorder in a mammal comprising administering to a mammal a therapeutically effective amount of a compound of formula (I) wherein A is cycloalkyl wherein the cycloalkyl is cyclohexyl; $R_1$ is $OR_2$; $R_2$ is hydrogen; and $R_A$, $R_B$, and $R_C$ are as defined in formula (I).

In another embodiment, the present invention relates to a method of treating epilepsy, migraine, or bipolar disorder in a mammal comprising administering to a mammal a therapeutically effective amount of a compound of formula (I) wherein A is cycloalkyl wherein the cycloalkyl is cyclohexyl; $R_1$ is $OR_2$; and $R_A$, $R_B$, $R_C$, and $R_2$ are hydrogen.

In another embodiment, the present invention relates to a method of treating epilepsy, migraine, or bipolar disorder in a mammal comprising administering to a mammal a therapeutically effective amount of a compound of formula (I) wherein A is cycloalkyl wherein the cycloalkyl is bicyclo[3.1.1]hept-2-yl, bicyclo[2.2.1]hept-2-yl, cycloheptyl, cyclopentyl, or cyclooctyl, wherein the cycloalkyl is optionally substituted with 1 or 2 alkyl groups; $R_1$ is $OR_2$; $R_2$ is hydrogen; and $R_A$, $R_B$, and $R_C$ are as defined in formula (I).

In another embodiment, the present invention relates to a method of treating epilepsy, migraine, or bipolar disorder in a mammal comprising administering to a mammal a therapeutically effective amount of a compound of formula (I) wherein A is bicycloalkyl; $R_1$ is $OR_2$; and $R_A$, $R_B$, $R_C$, and $R_2$ are as defined in formula (I).

In another embodiment, the present invention relates to a method of treating epilepsy, migraine, or bipolar disorder in a mammal comprising administering to a mammal a therapeutically effective amount of a compound of formula (I) wherein A is bicycloalkyl wherein the bicycloalkyl is bicyclo[3.2.0]hept-6-yl or decahydro-2-naphthalenyl wherein the bicycloalkyl is optionally substituted with 1 or 2 alkyl groups; $R_1$ is $OR_2$; $R_2$ is hydrogen; and $R_A$, $R_B$, and $R_C$ are as defined in formula (I).

In another embodiment, the present invention relates to a method of treating epilepsy, migraine, or bipolar disorder in a mammal comprising administering to a mammal a therapeutically effective amount of a compound of formula (I) wherein A is cycloalkyl; $R_1$ is $NR_3R_4$; and $R_A$, $R_B$, $R_C$, $R_3$, and $R_4$ are as defined in formula (I).

In another embodiment, the present invention relates to a method of treating epilepsy, migraine, or bipolar disorder in a mammal comprising administering to a mammal a therapeutically effective amount of a compound of formula (I) wherein A is cycloalkyl; $R_1$ is $NR_3R_4$; $R_3$ is hydrogen; and $R_4$ is alkyl, wherein a preferred alkyl is methyl; and $R_A$, $R_B$, and $R_C$ are as defined in formula (I).

In another embodiment, the present invention relates to a method of treating epilepsy, migraine, or bipolar disorder in a mammal comprising administering to a mammal a therapeutically effective amount of a compound of formula (I) wherein A is cycloalkyl wherein the cycloalkyl is cyclohexyl optionally substituted with 1, 2, or 3 alkyl groups; $R_1$ is $NR_3R_4$; $R_3$ is hydrogen; and $R_4$ is alkyl, wherein a preferred alkyl is methyl; and $R_A$, $R_B$, and $R_C$ are as defined in formula (I).

In another embodiment, the present invention relates to a method of treating epilepsy, migraine, or bipolar disorder in a mammal comprising administering to a mammal a therapeutically effective amount of a compound of formula (I) wherein A is cycloalkyl wherein the cycloalkyl is cyclohexyl; $R_1$ is $NR_3R_4$; $R_3$ is hydrogen; and $R_4$ is alkyl, wherein a preferred alkyl is methyl; and $R_A$, $R_B$, and $R_C$ are hydrogen.

In another embodiment, the present invention relates to a method of treating epilepsy, migraine, or bipolar disorder in a mammal comprising administering to a mammal a therapeutically effective amount of a compound of formula (I) wherein A is cycloalkyl wherein the cycloalkyl is cyclohexyl optionally substituted with 1, 2, 3, or 4 alkyl groups; $R_1$ is $NR_3R_4$; $R_4$ is hydrogen or $(NR_5R_6)$carbonylalkyl; $R_3$, $R_5$, and $R_6$ are hydrogen; and $R_A$, $R_B$, and $R_C$ are as defined in formula (I).

In another embodiment, the present invention relates to a method of treating epilepsy, migraine, or bipolar disorder in a mammal comprising administering to a mammal a therapeutically effective amount of a compound of formula (I) wherein A is cycloalkyl wherein the cycloalkyl is cyclohexyl; $R_1$ is $NR_3R_4$; $R_4$ is $(NR_5R_6)$carbonylalkyl; and $R_A$, $R_B$, $R_C$, $R_3$, $R_5$, and $R_6$ are hydrogen.

In another embodiment, the present invention relates to a method of treating epilepsy, migraine, or bipolar disorder in a mammal comprising administering to a mammal a therapeutically effective amount of a compound of formula (I) wherein A is cycloalkyl wherein the cycloalkyl is cyclohexyl; $R_1$ is $NR_3R_4$; $R_4$ is 2-amino-2-oxoethyl; and $R_A$, $R_B$, $R_C$, and $R_3$ are hydrogen.

In another embodiment, the present invention relates to a method of treating epilepsy, migraine, or bipolar disorder in a mammal comprising administering to a mammal a therapeutically effective amount of a compound of formula (I) wherein A is cycloalkyl wherein the cycloalkyl is cyclohexyl optionally substituted with 1, 2, 3, or 4 alkyl groups; $R_1$ is $NR_3R_4$; R is carboxyalkyl; $R_3$ is hydrogen; and $R_A$, $R_B$, and $R_C$ are as defined in formula (I).

In another embodiment, the present invention relates to a method of treating epilepsy, migraine, or bipolar disorder in a mammal comprising administering to a mammal a therapeutically effective amount of a compound of formula (I) wherein A is cycloalkyl wherein the cycloalkyl is cyclohexyl optionally substituted with 1, 2, 3, or 4 alkyl groups; $R_1$ is $NR_3R_4$; $R_4$ is hydroxyalkyl; $R_3$ is hydrogen; and $R_A$, $R_B$, and $R_C$ are as defined in formula (I).

In another embodiment, the present invention relates to a method of treating epilepsy, migraine, or bipolar disorder in a mammal comprising administering to a mammal a therapeutically effective amount of a compound of formula (I) wherein A is cycloalkyl wherein the cycloalkyl is cyclohexyl; $R_1$ is $NR_3R_4$; $R_4$ is hydroxyalkyl wherein the hydroxyalkyl is 2-hydroxypropyl; and $R_A$, $R_B$, $R_C$, and $R_3$ are hydrogen.

In another embodiment, the present invention relates to a method of treating epilepsy, migraine, or bipolar disorder in a mammal comprising administering to a mammal a therapeutically effective amount of a compound of formula (I) wherein A is cycloalkyl wherein the cycloalkyl is bicyclo[3.1.1]hept-2-yl, bicyclo[2.2.1]hept-2-yl, cycloheptyl, cyclopentyl, or cyclooctyl, wherein the cycloalkyl is optionally substituted with 1 or 2 alkyl groups; $R_1$ is $NR_3R_4$; $R_4$ is hydrogen or $(NR_5R_6)$carbonylalkyl; $R_3$, $R_5$, and $R_6$ are hydrogen; and $R_A$, $R_B$, and $R_C$ are as defined in formula (I).

In another embodiment, the present invention relates to a method of treating epilepsy, migraine, or bipolar disorder in a mammal comprising administering to a mammal a therapeutically effective amount of a compound of formula (I) wherein A is bicycloalkyl; $R_1$ is $NR_3R_4$; and $R_A$, $R_B$, $R_C$, $R_3$, and $R_4$ are as defined in formula (I).

In another embodiment, the present invention relates to a method of treating epilepsy, migraine, or bipolar disorder in a mammal comprising administering to a mammal a therapeutically effective amount of a compound of formula (I) wherein A is bicycloalkyl wherein the bicycloalkyl is bicyclo[3.2.0]hept-6-yl or decahydro-2-naphthalenyl, wherein the bicycloalkyl is optionally substituted with 1 or 2 alkyl groups; $R_1$ is $NR_3R_4$; $R_4$ is hydrogen or $(NR_5R_6)$carbonylalkyl; $R_3$, $R_5$, and $R_6$ are hydrogen; and $R_A$, $R_B$, and $R_C$ are as defined in formula (I).

In another embodiment, the present invention relates to a method of treating epilepsy, bipolar disorder, or migraine, in a mammal comprising administering to a mammal a therapeutically effective amount of (1R)—N-(2-amino-2-oxoethyl)spiro[2.5]octane-1-carboxamide.

In another embodiment, the present invention relates to a method of treating a psychiatric disorder, pain, or a movement disorder, in a mammal comprising administering to a mammal a therapeutically effective amount of a compound of formula (I).

In another embodiment, the present invention relates to a method of treating a psychiatric disorder, pain, or a movement disorder, in a mammal comprising administering to a mammal a therapeutically effective amount of (1R)—N-(2-amino-2-oxoethyl)spiro[2.5]octane-1-carboxamide.

In another embodiment, the present invention relates to a method of providing neuroprotection in a mammal comprising administering to a mammal a therapeutically effective amount of a compound of formula (I).

In another embodiment, the present invention relates to a method of providing neuroprotection in a mammal comprising administering to a mammal a therapeutically effective amount of (1R)—N-(2-amino-2-oxoethyl)spiro[2.5]octane-1-carboxamide.

Representative compounds of formula (I) include, but are not limited to:
spiro[2.5]octane-1-carboxylic acid;
spiro[2.5]octane-1-carboxamide;
(1S)—N-[(1S)-2-amino-1-methyl-2-oxoethyl]spiro[2.5]octane-1-carboxamide;
(1R)—N-[(1S)-2-amino-1-methyl-2-oxoethyl]spiro[2.5]octane-1-carboxamide;
(1S)-spiro[2.5]octane-1-carboxylic acid;
(1S)-spiro[2.5]octane-1-carboxamide;
(1R)-spiro[2.5]octane-1-carboxylic acid;
(1R)-spiro[2.5]octane-1-carboxamide;
spiro[2.4]heptane-1-carboxylic acid;
spiro[2.4]heptane-1-carboxamide;
N-(2-amino-2-oxoethyl)spiro[2.4]heptane-1-carboxamide;
(1R,5S)-6,6-dimethylspiro[bicyclo[3.1.1]heptane-2,1'-cyclopropane]-2'-carboxylic acid;
(1R,5S)-6,6-dimethylspiro[bicyclo[3.1.1]heptane-2,1'-cyclopropane]-2'-carboxamide;
(1R,5S)—N-(2-amino-2-oxoethyl)-6,6-dimethylspiro[bicyclo[3.1.1]heptane-2,1'-cyclopropane]-2'-carboxamide;
2-methylspiro[2.5]octane-1-carboxylic acid;
2-methylspiro[2.5]octane-1-carboxamide;

N-(2-amino-2-oxoethyl)-2-methylspiro[2.5]octane-1-carboxamide;
5,7-dimethylspiro[2.5]octane-1-carboxylic acid;
5,7-dimethylspiro[2.5]octane-1-carboxamide;
N-(2-amino-2-oxoethyl)-5,7-dimethylspiro[2.5]octane-1-carboxamide;
6-tert-butylspiro[2.5]octane-1-carboxylic acid;
6-tert-butylspiro[2.5]octane-1-carboxamide;
N-(2-amino-2-oxoethyl)-6-tert-butylspiro[2.5]octane-1-carboxamide;
2-methylspiro[2.4]heptane-1-carboxylic acid;
2-methylspiro[2.4]heptane-1-carboxamide;
N-(2-amino-2-oxoethyl)-2-methylspiro[2.4]heptane-1-carboxamide;
3,3-dimethylspiro[bicyclo[2.2.1]heptane-2,1'-cyclopropane]-2'-carboxylic acid;
3,3-dimethylspiro[bicyclo[2.2.1]heptane-2,1'-cyclopropane]-2'-carboxamide;
N-(2-amino-2-oxoethyl)-3,3-dimethylspiro[bicyclo[2.2.1]heptane-2,1'-cyclopropane]-2'-carboxamide;
4-methylspiro[bicyclo[3.2.0]heptane-6,1'-cyclopropane]-2'-carboxylic acid;
4-methylspiro[bicyclo[3.2.0]heptane-6,1'-cyclopropane]-2'-carboxamide;
N-(2-amino-2-oxoethyl)-4-methylspiro[bicyclo[3.2.0]heptane-6,1'-cyclopropane]-2'-carboxamide;
spiro[bicyclo[2.2.1]heptane-2,1'-cyclopropane]-2'-carboxylic acid;
spiro[bicyclo[2.2.1]heptane-2,1'-cyclopropane]-2'-carboxamide;
N-(2-amino-2-oxoethyl)spiro[bicyclo[2.2.1]heptane-2,1'-cyclopropane]-2'-carboxamide;
spiro[2.6]nonane-1-carboxylic acid;
spiro[2.6]nonane-1-carboxamide;
N-(2-amino-2-oxoethyl)spiro[2.6]nonane-1-carboxamide;
(4S,7R)-4-isopropyl-7-methylspiro[2.5]octane-1-carboxylic acid;
(4S,7R)-4-isopropyl-7-methylspiro[2.5]octane-1-carboxamide;
(4S,7R)—N-(2-amino-2-oxoethyl)-4-isopropyl-7-methylspiro[2.5]octane-1-carboxamide;
octahydro-1'H-spiro[cyclopropane-1,2'-naphthalene]-2-carboxylic acid;
octahydro-1'H-spiro[cyclopropane-1,2'-naphthalene]-2-carboxamide;
N-(2-amino-2-oxoethyl)octahydro-1'H-spiro[cyclopropane-1,2'-naphthalene]-2-carboxamide;
N-(3-amino-3-oxopropyl)spiro[2.5]octane-1-carboxamide;
spiro[2.7]decane-1-carboxylic acid;
spiro[2.7]decane-1-carboxamide;
N-(2-amino-2-oxoethyl)spiro[2.7]decane-1-carboxamide;
5,5,7,7-tetramethylspiro[2.5]octane-1-carboxylic acid;
5,5,7,7-tetramethylspiro[2.5]octane-1-carboxamide;
N-(2-amino-2-oxoethyl)-5,5,7,7-tetramethylspiro[2.5]octane-1-carboxamide;
[(spiro[2.5]oct-1-ylcarbonyl)amino]acetic acid;
{[(1S)-spiro[2.5]oct-1-ylcarbonyl]amino}acetic acid;
{[(1R)-spiro[2.5]oct-1-ylcarbonyl]amino}acetic acid;
spiro[bicyclo[3.2.0]heptane-6,1'-cyclopropane]-2'-carboxylic acid;
spiro[bicyclo[3.2.0]heptane-6,1'-cyclopropane]-2'-carboxamide;
N-(2-amino-2-oxoethyl)spiro[bicyclo[3.2.0]heptane-6,1'-cyclopropane]-2'-carboxamide;
(1R)—N-[(2R)-2-hydroxypropyl]spiro[2.5]octane-1-carboxamide;
(1S)—N-[(2R)-2-hydroxypropyl]spiro[2.5]octane-1-carboxamide;
(1R)—N-[(2S)-2-hydroxypropyl]spiro[2.5]octane-1-carboxamide;
(1S)—N-[(2S)-2-hydroxypropyl]spiro[2.5]octane-1-carboxamide;
(1R)—N-methylspiro[2.5]octane-1-carboxamide; and
(1S)—N-methylspiro[2.5]octane-1-carboxamide; or a pharmaceutically acceptable prodrug thereof.

Preferred compounds of formula (I) include
N-(2-amino-2-oxoethyl)spiro[2.5]octane-1-carboxamide;
(1S)—N-(2-amino-2-oxoethyl)spiro[2.5]octane-1-carboxamide; and
(1R)—N-(2-amino-2-oxoethyl)spiro[2.5]octane-1-carboxamide or a pharmaceutically acceptable prodrug thereof.

In another embodiment, the present invention relates to compounds of formula (II)

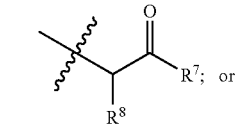

(II)

or a pharmaceutically acceptable prodrug thereof, wherein
A is cycloalkyl or bicycloalkyl wherein the cycloalkyl and bicycloalkyl are optionally substituted with 1, 2, 3, or 4 alkyl groups;
$R_A$, $R_B$, and $R_C$ are independently hydrogen or alkyl;
$R_3$ is alkenyl, alkynyl, alkoxycarbonylalkyl, carboxyalkyl, cycloalkyl, cycloalkylalkyl, heterocycle, heterocyclealkyl, hydroxyalkyl, $(NR_5R_6)$alkyl, or $(NR_5R_6)$carbonylalkyl;
$R_4$ is hydrogen, alkenyl, alkyl, alkynyl, alkoxycarbonylalkyl, carboxyalkyl, cycloalkyl, cycloalkylalkyl, heterocycle, heterocyclealkyl, hydroxyalkyl, $(NR_5R_6)$alkyl, or $(NR_5R_6)$carbonylalkyl, or $R_3$ and $R_4$ taken together with the nitrogen atom to which they are attached form a heterocycle wherein the heterocycle is azepanyl, azetidinyl, aziridinyl, morpholinyl, piperazinyl, piperidinyl, pyrrolidinyl, or thiomorpholinyl;
$R_5$ and $R_6$ are independently hydrogen, alkenyl, alkyl, alkynyl, alkoxycarbonylalkyl, aryl, arylalkyl, cycloalkyl, cycloalkylalkyl, heterocycle, or heterocyclealkyl;
$R_7$ is alkoxy, alkyl, hydroxy, or —$NR_5R_6$;
$R_8$ is alkenyl, alkoxyalkyl, alkoxycarbonylalkyl, alkylthioalkyl, alkynyl, aryl, arylalkyl, carboxyalkyl, cycloalkyl, cycloalkylalkyl, heterocycle, heterocyclealkyl, hydroxyalkyl, mercaptoalkyl, $(NR_5R_6)$alkyl, $(NR_5R_6)$carbonylalkyl, or —$(CH_2)_nNHC(=NH)NH_2$; and
n is an integer from 1 to 6.

In another embodiment, the present invention relates to a compound of formula (II) wherein A is cycloalkyl optionally substituted with 1, 2, 3, or 4 alkyl groups; and $R_A$, $R_B$, $R_C$, $R_3$, and $R_4$ are as defined in formula (II).

In another embodiment, the present invention relates to a compound of formula (II) wherein A is cycloalkyl wherein the cycloalkyl is cyclohexyl optionally substituted with 1, 2, 3, or 4 alkyl groups; $R_3$ is alkyl; $R_4$, $R_5$, and $R_6$ are hydrogen; and $R_A$, $R_B$, and $R_C$ are as defined in formula (II).

In another embodiment, the present invention relates to a compound of formula (II) wherein A is cycloalkyl wherein the cycloalkyl is cyclohexyl; $R_3$ is alkyl, wherein the preferred alkyl group is methyl; and $R_A$, $R_B$, $R_C$, $R_4$, $R_5$, and $R_6$ are hydrogen.

In another embodiment, the present invention relates to a compound of formula (II) wherein A is cycloalkyl wherein the cycloalkyl is cyclohexyl optionally substituted with 1, 2, 3, or 4 alkyl groups; $R_3$ is $(NR_5R_6)$carbonylalkyl; $R_4$, $R_5$, and $R_6$ are hydrogen; and $R_A$, $R_B$, and $R_C$ are as defined in formula (II).

In another embodiment, the present invention relates to a compound of formula (II) wherein A is cycloalkyl wherein the cycloalkyl is cyclohexyl; $R_3$ is $(NR_5R_6)$carbonylalkyl; $R_4$, $R_5$, and $R_6$ are hydrogen; and $R_A$, $R_B$, and $R_C$ are as defined in formula (II).

In another embodiment, the present invention relates to a compound of formula (II) wherein A is cycloalkyl wherein the cycloalkyl is cyclohexyl; $R_3$ is $(NR_5R_6)$carbonylalkyl; and $R_A$, $R_B$, $R_C$, $R_4$, $R_5$, and $R_6$ are hydrogen.

In another embodiment, the present invention relates to a compound of formula (II) wherein A is cycloalkyl wherein the cycloalkyl is cyclohexyl; $R_3$ is $(NR_5R_6)$carbonylalkyl wherein the $(NR_5R_6)$carbonylalkyl is 2-amino-2-oxoethyl; and $R_A$, $R_B$, $R_C$, $R_4$, $R_5$, and $R_6$ are hydrogen.

In another embodiment, the present invention relates to a compound of formula (II) wherein A is cycloalkyl wherein the cycloalkyl is cyclohexyl optionally substituted with 1, 2, 3, or 4 alkyl groups; $R_3$ is carboxyalkyl or hydroxyalkyl; $R_4$ is hydrogen; and $R_A$, $R_B$, and $R_C$ are as defined in formula (II).

In another embodiment, the present invention relates to a compound of formula (II) wherein A is cycloalkyl wherein the cycloalkyl is cyclohexyl; $R_3$ is carboxyalkyl or hydroxyalkyl; $R_4$, $R_5$, and $R_6$ are hydrogen; and $R_A$, $R_B$, and $R_C$ are as defined in formula (II).

In another embodiment, the present invention relates to a compound of formula (II) wherein A is cycloalkyl wherein the cycloalkyl is cyclohexyl; $R_3$ is carboxyalkyl or hydroxyalkyl; and $R_A$, $R_B$, $R_C$, $R_4$, $R_5$, and $R_6$ are hydrogen.

In another embodiment, the present invention relates to a compound of formula (II) wherein A is cycloalkyl wherein the cycloalkyl is cyclohexyl; $R_3$ is hydroxyalkyl; and $R_A$, $R_B$, $R_C$, $R_4$, $R_5$, and $R_6$ are hydrogen.

In another embodiment, the present invention relates to a compound of formula (II) wherein A is cycloalkyl wherein the cycloalkyl is cyclohexyl; $R_3$ is hydroxyalkyl wherein the hydroxyalkyl is 2-hydroxypropyl; and $R_A$, $R_B$, $R_C$, $R_4$, $R_5$, and $R_6$ are hydrogen.

In another embodiment, the present invention relates to a compound of formula (II) wherein A is cycloalkyl wherein the cycloalkyl is bicyclo[3.1.1]hept-2-yl, bicyclo[2.2.1]hept-2-yl, cycloheptyl, cyclopentyl, or cyclooctyl, wherein the cycloalkyl is optionally substituted with 1 or 2 alkyl groups; $R_3$ is $(NR_5R_6)$carbonylalkyl; $R_4$, $R_5$, and $R_6$ are hydrogen; and $R_A$, $R_B$, and $R_C$ are as defined in formula (II).

In another embodiment, the present invention relates to a compound of formula (II) wherein A is bicycloalkyl optionally substituted with 1, 2, 3, or 4 alkyl groups; and $R_A$, $R_B$, $R_C$, $R_3$, and $R_4$ are as defined in formula (II).

In another embodiment, the present invention relates to a compound of formula (II) wherein A is bicycloalkyl wherein the bicycloalkyl is bicyclo[3.2.0]hept-6-yl or decahydro-2-naphthalenyl, wherein the bicycloalkyl is optionally substituted with 1 or 2 alkyl groups; $R_3$ is $(NR_5R_6)$carbonylalkyl; $R_4$, $R_5$, and $R_6$ are hydrogen; and $R_A$, $R_B$, and $R_C$ are as defined in formula (II).

DEFINITION OF TERMS

As used throughout this specification and the appended claims, the following terms have the following meanings:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein, means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl" as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkyl group, as defined herein. Representative examples of alkoxycarbonylalkyl include, but are not limited to, 3-methoxycarbonylpropyl, 4-ethoxycarbonylbutyl, and 2-tert-butoxycarbonylethyl.

The term "alkoxysulfonyl" as used herein, means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonylalkyl" as used herein, means an alkylcarbonyl group, as defined herein, appended to the parent molecular moiety through an alkyl group, as defined herein. Representative examples of alkylcarbonylalkyl include, but are not limited to, 2-oxopropyl, 3,3-dimethyl-2-oxopropyl, 3-oxobutyl, and 3-oxopentyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylene" means a divalent group derived from a straight or branched chain hydrocarbon of from 1 to 10 carbon atoms. Representative examples of alkylene include, but are not limited to, —CH$_2$—, —CH(CH$_3$)—, —C(CH$_3$)$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkylthioalkyl" as used herein, means an alkylthio group, as defined herein, appended to the parent molecular moiety through an alkyl group, as defined herein. Representative examples of alkylthioalkyl include, but are not limited, methylthiomethyl and 2-(ethylthio)ethyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl" as used herein, means a monocyclic-ring system, or a bicyclic- or a tricyclic-fused ring system wherein one or more of the fused rings are aromatic. Representative examples of aryl include, but are not limited to, anthracenyl, azulenyl, fluorenyl, 2,3-dihydroindenyl, indenyl, naphthyl, phenyl, and tetrahydronaphthyl.

The aryl groups of this invention are optionally substituted with 1, 2, or 3 substituents independently selected from the group consisting of alkenyl, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, carboxy, carboxyalkyl, cyano, cyanoalkyl, ethylenedioxy, formyl, haloalkoxy, haloalkyl, halogen, hydroxy, hydroxyalkyl, mercapto, methylenedioxy, nitro, —NR$_D$R$_E$, and (NR$_D$R$_E$)carbonyl.

The term "arylalkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "bicycloalkyl" as used herein, means a cycloalkyl group, defined as a monocyclic ring system, fused to another cycloalkyl group, defined as a monocyclic ring system. Representative examples of bicycloalkyl, include, but are not limited to, bicyclo[2.2.0]cyclohexane, bicyclo[3.2.0]heptane, bicyclo[4.2.0]octane, decahydronaphthalenyl, octahydro-1H-indenyl, and octahydropentalenyl.

The bicycloalkyl groups of the present invention are optionally substituted with 1, 2, 3, or 4 substituents selected from the group consisting of alkenyl, alkoxy, alkoxycarbonyl, alkyl, alkylcarbonyl, alkylthio, alkynyl, carboxy, cyano, formyl, haloalkoxy, haloalkyl, halogen, hydroxy, oxo, mercapto, —NR$_D$R$_E$, and (NR$_D$R$_E$)carbonyl.

The term "carbonyl" as used herein, means a —C(O)— group.

The term "carboxy" as used herein, means a —CO$_2$H group.

The term "carboxyalkyl" as used herein, means a carboxy group, as defined herein, appended to the parent molecular moiety through an alkyl group, as defined herein. Representative examples of carboxyalkyl include, but are not limited to, carboxymethyl, 2-carboxyethyl, and 3-carboxypropyl.

The term "cyano" as used herein, means a —CN group.

The term "cyanoalkyl" as used herein, means a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "cycloalkyl" as used herein, means a monocyclic ring system or a bridged monocyclic ring system. Monocyclic ring systems are exemplified by a saturated cyclic hydrocarbon group containing from 3 to 8 carbon atoms. Examples of monocyclic ring systems include cyclopropyl, cyclobutyl, cyclopentyl, cyclohexyl, cycloheptyl, and cyclooctyl. Bridged monocyclic ring systems are exemplified by a monocyclic ring system in which two non-adjacent carbon atoms of the monocyclic ring are linked by an alkylene group, as defined herein. Representative examples of bridged monocyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane.

The cycloalkyl groups of the present invention are optionally substituted with 1, 2, 3, or 4 substituents selected from the group consisting of alkenyl, alkoxy, alkoxycarbonyl, alkyl, alkylcarbonyl, alkylthio, alkynyl, carboxy, cyano, formyl, haloalkoxy, haloalkyl, halogen, hydroxy, oxo, mercapto, —NR$_D$R$_E$, and (NR$_D$R$_E$)carbonyl.

The term "cycloalkylalkyl" as used herein, means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "ethylenedioxy" as used herein, means a —O(CH$_2$)$_2$O— group wherein the oxygen atoms of the ethylenedioxy group are attached to the parent molecular moiety through one carbon atom forming a 5 membered ring or the oxygen atoms of the ethylenedioxy group are attached to the parent molecular moiety through two adjacent carbon atoms forming a six membered ring.

The term "formyl" as used herein, means a —C(O)H group.

The term "halo" or "halogen" as used herein, means —Cl, —Br, —I or —F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heterocycle" or "heterocyclic" as used herein, means a monocyclic, bicyclic, or tricyclic ring system. Monocyclic ring systems are exemplified by any 3- or 4-membered ring containing a heteroatom independently selected from the group consisting of oxygen, nitrogen and sulfur; or a 5-, 6- or 7-membered ring containing one, two or three heteroatoms wherein the heteroatoms are independently selected from the group consisting of nitrogen, oxygen and sulfur. The 5-membered ring has from 0-2 double bonds and the 6- and 7-membered ring have from 0-3 double bonds. Representative examples of monocyclic ring systems include, but are not limited to, azetidinyl, azepanyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, piperidinyl, pyranyl, pyrazinyl, pyrazolyl, pyrazolinyl, pyrazolidinyl, pyridinyl, pyrimidinyl, pyridazinyl, pyrrolyl, pyrrolinyl, pyrrolidinyl, tetrahydrofuranyl, tetrahydrothienyl, tetrazinyl, tetrazolyl, thiadiazolyl, thiadiazolinyl, thiadiazolidinyl, thienyl, thiomorpholinyl, 1,1-dioxidothiomorpholinyl(thiomorpholine sulfone), thiopyranyl, triazinyl, triazolyl, and trithianyl. Bicyclic ring systems are exemplified by any of the above monocyclic ring systems fused to an aryl group as defined herein, a cycloalkyl group as defined herein, or another monocyclic ring system. Representative examples of bicyclic ring systems include but are not limited to, for example, benzimidazolyl, benzodioxinyl, benzothiazolyl, benzothienyl, benzotriazolyl, benzoxazolyl, benzofuranyl, benzopyranyl, benzothiopyranyl, cinnolinyl, indazolyl, indolyl, 2,3-dihydroindolyl, indolizinyl, naphthyridinyl, isobenzofuranyl, isobenzothienyl, isoindolyl, isoquinolinyl, phthalazinyl, pyranopyridinyl, quinolinyl, quinolizinyl, quinoxalinyl, quinazolinyl, tetrahydroisoquinolinyl, tetrahydroquinolinyl, and thiopyranopyridinyl. Tricyclic rings systems are exemplified by any of the above bicyclic ring systems fused to an aryl group as defined herein, a cycloalkyl group as defined herein, or a monocyclic ring system. Representative examples of tricyclic ring systems include, but are not limited to, acridinyl, carbazolyl, carbolinyl, dibenzo[b,d]furanyl, dibenzo[b,d]thienyl, naphtho[2,3-b]furan, naphtho[2,3-b]thienyl, phenazinyl, phenothiazinyl, phenoxazinyl, thianthrenyl, thioxanthenyl and xanthenyl.

The heterocycles of this invention are optionally substituted with 1, 2, or 3 substituents independently selected from the group consisting of alkenyl, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, ethylenedioxy, formyl, haloalkoxy, haloalkyl, halogen, hydroxy, hydroxyalkyl, mercapto, methylenedioxy, nitro, oxo, —$NR_DR_E$, and ($NR_DR_E$)carbonyl.

The term "heterocyclealkyl" as used herein, means a heterocycle, as defined herein, appended to the parent molecular moiety through an alkyl group, as defined herein. Representative examples of heterocyclealkyl include, but are not limited to, pyridin-3-ylmethyl and 2-pyrimidin-2-ylpropyl.

The term "hydroxy" as used herein, means an —OH group.

The term "hydroxyalkyl" as used herein, means at least one hydroxy group, as defined herein, appended to the parent molecular moiety through an alkyl group, as defined herein. Representative examples of hydroxyalkyl include, but are not limited to, hydroxymethyl, 2-hydroxyethyl, 2-hydroxypropyl, 3-hydroxypropyl, 2,3-dihydroxypentyl, and 2-ethyl-4-hydroxyheptyl.

The term "mercapto" as used herein, means a —SH group.

The term "mercaptoalkyl" as used herein, means a mercapto group, as defined herein, appended to the parent molecular moiety through an alkyl group, as defined herein. Representative examples of mercaptoalkyl include, but are not limited to, 2-mercaptoethyl and 3-mercaptopropyl.

The term "methylenedioxy" as used herein, means a —OCH$_2$O— group wherein the oxygen atoms of the methylenedioxy are attached to the parent molecular moiety through two adjacent carbon atoms.

The term "nitro" as used herein, means a —NO$_2$ group.

The term "—$NR_DR_E$" as used herein, means two groups, $R_D$ and $R_E$, which are appended to the parent molecular moiety through a nitrogen atom. $R_D$ and $R_E$ are each independently selected from the group consisting of hydrogen, alkenyl, alkoxycarbonyl, alkoxysulfonyl, alkyl, alkylcarbonyl, alkylsulfonyl, alkynyl, and formyl. Representative examples of —$NR_DR_E$ include, but are not limited to, amino, acetylamino, methylamino, dimethylamino, ethylamino, ethylmethylamino, benzylamino, methoxysulfonylamino, methylsulfonylamino, ethoxycarbonylamino, and tert-butoxycarbonylamino.

The term "($NR_DR_E$)carbonyl" as used herein, means a —$NR_DR_E$ group, as defined herein, appended to the parent molecular moiety through a carbonyl group, as defined herein. Representative examples of ($NR_DR_E$)carbonyl include, but are not limited to, aminocarbonyl, (methylamino)carbonyl, (dimethylamino)carbonyl and (ethylmethylamino)carbonyl.

The term "($NR_5R_6$)alkyl" as used herein, means a —$NR_5R_6$ group, as defined herein, appended to the parent molecular moiety through an alkyl group, as defined herein. Representative examples of ($NR_5R_6$)alkyl include, but are not limited to, 2-aminoethyl, 2-(dimethylamino)ethyl, and 3-aminopropyl.

The term "($NR_5R_6$)carbonyl" as used herein, means a —$NR_5R_6$ group, as defined herein, appended to the parent molecular moiety through a carbonyl group, as defined herein. Representative examples of ($NR_5R_6$)carbonyl include, but are not limited to, aminocarbonyl, (methylamino)carbonyl, (dimethylamino)carbonyl, and (ethylmethylamino)carbonyl.

The term "($NR_5R_6$)carbonylalkyl" as used herein, means a ($NR_5R_6$)carbonyl group, as defined herein, appended to the parent molecular moiety through an alkyl group, as defined herein. Representative examples of ($NR_5R_6$)carbonylalkyl include, but are not limited to, 2-amino-2-oxoethyl, 2-methylamino-2-oxoethyl, and 2-dimethylamino-2-oxoethyl.

The term "oxo" as used herein, means a =O moiety.

The term "sulfonyl" as used herein, means a —SO$_2$— group.

Compounds of the present invention were named by ACD/ChemSketch version 5.0 (developed by Advanced Chemistry Development, Inc., Toronto, ON, Canada) or were given names consistent with ACD nomenclature.

Compounds of the present invention can exist as stereoisomers, wherein asymmetric or chiral centers are present. Stereoisomers are designated "R" or "S," depending on the configuration of substituents around the chiral carbon atom. The terms "R" and "S" used herein are configurations as defined in IUPAC 1974 Recommendations for Section E, Fundamental Stereochemistry, Pure Appl. Chem., (1976), 45: 13-30. The present invention contemplates various stereoisomers and mixtures thereof and are specifically included within the scope of this invention. Stereoisomers include enantiomers, diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution, a technique well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) direct separation of the mixture of optical enantiomers on chiral chromatographic columns, or (3) formation of a diastereomeric salt followed by selective recrystallization of one of the diastereomeric salts.

ABBREVIATIONS

Abbreviations which have been used in the descriptions of the schemes and the examples that follow are: DMSO for dimethylsulfoxide and TEA for triethylamine.

Preparation of Compounds of The Invention

The compounds of the present invention can be prepared by a variety of synthetic routes. Representative procedures are shown in Scheme 1 and 2.

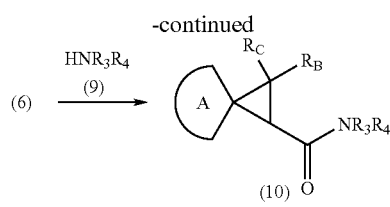

Spirocycles of general formula (8) and (10), wherein A, $R_B$, $R_C$, $R_2$, $R_3$, and $R_4$ are as defined in formula (I), can be prepared as described in Scheme 1. Alcohols of general formula (1), purchased or prepared using methodology known to those of skill in the art, can be oxidized under Swern conditions, oxalyl chloride/DMSO/TEA, or treated with an oxidizing agent, including but not limited to, pyridinium chlorochromate, pyridinium dichromate, $MnO_2$, or a peracid such as meta-chloroperoxybenzoic acid, to provide ketones of general formula (2). Ketones of general formula (2) can be treated with phosphorous ylenes or ylides of general formula (3) to provide alkenes of general formula (4). Alkenes of general formula (4) can be treated with ethyl diazoacetate and copper powder to provide spirocyclic compounds of general formula (5). Esters of general formula (5) can be saponified to provide acids of general formula (6). Acids of general formula (6) can be treated with thionyl chloride and an alcohol of general formula (7) to provide esters of general formula (8). Acids of general formula (6) can also be treated with amines of general formula (9) and a coupling reagent, including but not limited to, 1,1'-carbonyldiimidazole (CDI), 1,1'-thiocarbonyldiimidazole, 1,3-dicyclohexylcarbodiimide, 1-ethyl-3-[3-(dimethylamino)propyl]carbodiimide hydrochloride, or thionylchloride, to provide amides of general formula (10).

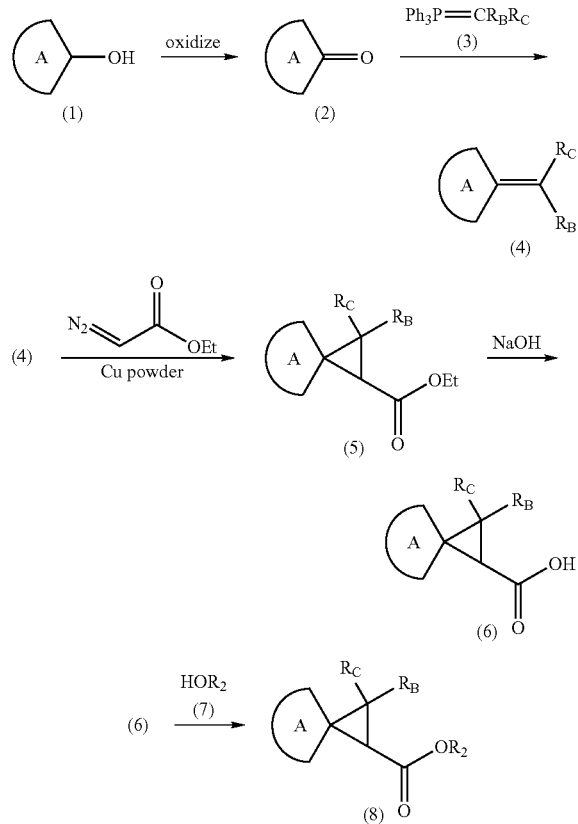

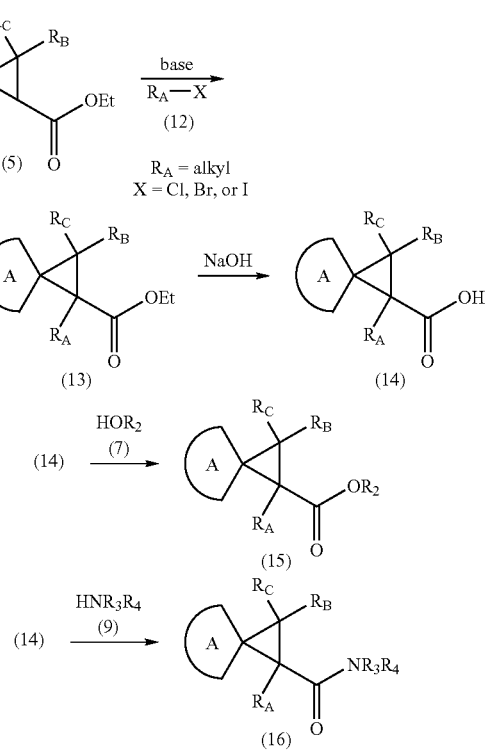

Spirocycles of general formula (15) and (16), wherein A, $R_B$, $R_C$, $R_2$, $R_3$, and $R_4$ are as defined in formula (I) and $R_4$ is alkyl as defined herein, can be prepared as described in Scheme 2. Spirocycles of general formula (5), prepared as described in Scheme 1, can be treated with a base, including but not limited to, lithium diisopropylamide, sodium bis(trimethylsilyl)amide, potassium bis(trimethylsilyl)amide, lithium bis(trimethylsilyl)amide, or sodium hydride and an alkyl halide of general formula (12), including but not limited to, iodomethane or iodoethane in a solvent, including but not limited to, THF or DMF to provide esters of general formula (13). Esters of general formula (13) can be processed as described in Scheme 1 to provide spirocycles of general formula (15) and (16).

Example 1

Spiro[2.5]octane-1-carboxylic acid

Example 1A

Ethyl spiro[2.5]octane-1-carboxylate

A 250 mL round-bottom flask was charged with methylenecyclohexane (20.0 g, 0.21 mol, commercially available from Aldrich), copper powder (2.8 g), methyl cyclohexane (50 mL) and heated to 105° C. Ethyl diazoacetate (26 g, 0.23 mol, commercially available from Aldrich) was added dropwise over an 8-hour period while maintaining the temperature between 100-105° C. Upon complete addition, the mixture was heated an additional 2 hours, allowed to cool to ambient temperature and stirred for an additional 12 hours. The reaction mixture was filtered and concentrated under reduced pressure to afford the title compound which was used without further purification.

Example 1B

Spiro[2.5]octane-1-carboxylic acid

The product from Example 1A in 100 mL of water was treated with NaOH (11.4 g, 0.29 mol) and heated at reflux for 8 hours. The reaction mixture was allowed to cool to ambient temperature and extracted with diethyl ether (2×100 mL). The aqueous layer was acidified to pH 3 by careful addition of concentrated HCl and extracted with diethyl ether (3×100 mL). The ethereal extracts were combined and concentrated under reduced pressure to afford an oil that was distilled under vacuum (120° C., 60 torr) to provide the title compound as a clear oil. $^1$H NMR (CDCl$_3$, 300 MHz) δ 11.95 (s, 1H), 1.30-1.60 (m, 11H), 1.13 (dd, 1H), 0.90 (dd, 1H); $^{13}$C NMR (CDCl$_3$, 100 MHz) δ 179.6, 37.5, 32.1, 28.8, 26.0, 25.9, 25.6, 21.6; MS m/z 172 (M+NH$_4$)$^+$.

Example 2

Spiro[2.5]octane-1-carboxamide

A 100 mL flask was charged with the product from Example 1B (2.8 g, 18 mmol), 1,1'-carbonyldiimidazole (2.9 g, 18 mmol) and ethyl acetate (20 mL). The mixture was stirred under nitrogen at ambient temperature for 4 hours, then 20 mL of concentrated ammonium hydroxide was added and the mixture stirred for 18 hours. The mixture was diluted with ethyl acetate (50 mL) and the layers were separated. The organic extract was washed with water (3×15 mL), dried over magnesium sulfate and concentrated under reduced pressure. The crude product was treated with carbon and recrystallized from aqueous methanol to provide the title compound as white crystals (3 g, 78% yield). $^1$H NMR (CDCl$_3$, 300 MHz) δ 5.55 (s, 2H), 1.3-1.7 (m, 10H), 1.28 (dd, 1H), 1.11 (t, 1H), 0.75 (dd, 1H); $^{13}$C NMR (CDCl$_3$, 100 MHz) δ 174.1, 37.6, 28.9, 28.6, 27.5, 26.2, 25.8, 25.6, 19.4; MS m/z 154 (M+H)$^+$.

Example 3

N-(2-amino-2-oxoethyl)spiro[2.5]octane-1-carboxamide

The product from Example 1B (420 g, 2.72 mol) and 1,1'-carbonyldiimidazole (530 g, 3.27 mol) were combined in ethyl acetate (8.9 Kg) at ambient temperature and stirred for 2 hours. The mixture was treated with water (50 mL) and 2-aminoacetamide hydrochloride (368 g, 3.27 mol, purchased from Aldrich), heated at 65° C. for 10 hours, allowed to cool to room temperature, diluted with H$_2$O (4.9 Kg) and heptane (1.35 Kg), and cooled to 10° C. resulting in formation of a solid. The solid was collected by filtration and washed with a mixture of H$_2$O (440 g) and ethyl acetate (350 g). The resulting wet cake was slurried with H$_2$O (2.0 Kg), filtered (550 g heptane wash) and dried to afford the title compound. $^1$H NMR (d$_6$-DMSO, 300 MHz) δ 8.10 (t, 1H), 7.21 (s, 1H), 6.95 (s, 1H), 3.62 (dq, 2H), 1.1-1.6 (m, 11H), 0.85 (dd, 1H), 0.61 (dd, 1H); $^{13}$C NMR (CDCl$_3$, 100 MHz) δ 171.2, 170.8, 42.0, 36.9, 28.2, 26.7, 25.8, 25.2, 18.1; MS m/z 211 (M+H)$^+$.

Example 4

(1S)—N-[(1S)-2-amino-1-methyl-2-oxoethyl]spiro[2.5]octane-1-carboxamide

A 1000 mL flask was charged with the product from Example 1B (47.8 g, 0.31 mol), 1,1'-carbonyldiimidazole (60.8 g, 0.37 mol) and 500 mL of ethyl acetate. The mixture was stirred at ambient temperature for 2 hours then (2S)-2-aminopropanamide hydrochloride (46.7 g, 0.70 mol, commercially available from Aldrich) and 30 mL of water were charged to the flask. The reaction mixture was heated at 65° C. for 19 hours. After cooling to ambient temperature, the reaction flask was charged with 500 mL of water and stirred for 4 hours resulting in formation of a crystalline solid. The solid was filtered, rinsed with 100 mL of ethyl acetate, and dried to provide the title compound in 97% diastereomeric excess (de) as determined by HPLC: Zobax RX-C8 column, 5 μm, 4.6× 250 mm; detector λ=205 nm, eluted with 15% CH$_3$CN/0.03 M KH$_2$PO$_4$ for 10 minutes then 35% CH$_3$CN/0.03 M KH$_2$PO$_4$ over 15 minutes; retention time 20.01 minutes. Stereochemistry was determined by x-ray crystallography. X-ray data: MW=224.30, C$_{12}$H$_{20}$N$_2$O$_2$, crystal dimensions 0.40X0.40X0.40 mm, primitive orthorhombic, P2$_1$2$_1$2$_1$ (#19), a=6.9845(9) Å, b=8.642(1) Å, c=22.081(3) Å, V=1332.8(3) Å$^3$, Z=4, D$_{calc}$=1.118 g/cm$^3$. Crystallographic data were collected using MoKα graphite monochromated radiation (λ=0.71069 Å). Refinement of the structure using full matrix least squares refinement of 2049 observed reflections (I>3.00σ(I)) and 145 variable parameters and converged with unweighted and weighted agreement factors of R=0.068 and R$_w$=0.075. $^1$H NMR (DMSO-d$_6$, 300 MHz) δ 8.00 (d, 1H), 7.19 (s, 1H), 6.91 (s, 1H), 4.22 (p, 1H), 1.50 (dd), 1.3-1.6 (m, 10H), 1.19 (d, 3H), 0.85 (dd), 0.59 (dd, 1H); $^{13}$C NMR (DMSO-d$_6$, 100 MHz) δ 174.1, 169.8, 47.9, 37.0, 28.3, 28.1, 26.7, 25.9, 25.2, 25.2, 18.5, 18.1; MS m/z 225 (M+H)$^+$.

Example 5

(1R)—N-[(1S)-2-amino-1-methyl-2-oxoethyl]spiro[2.5]octane-1-carboxamide

The remaining mother liquor from Example 4 was distilled to dryness and the residue dissolved in methanol/water with heating to 60° C. The solution was cooled to 30° C. resulting in formation of a crystalline solid. The solid was collected by filtration and dried to afford the title compound in 93% de (HPLC: Zobax RX-C8 column, 5 μm, 4.6×250 mm; detector λ=205 nm, eluted with 15% $CH_3CN$/0.03 M $KH_2PO_4$ for 10 minutes then 35% $CH_3CN$/0.03 M $KH_2PO_4$ over 15 minutes, retention time 20.33.) $^1$H NMR (DMSO-$d_6$, 300 MHz) δ 8.05 (d, 1H), 7.25 (s, 1H), 6.95 (s, 1H), 4.22 (p, 1H), 1.50 (dd), 1.3-1.6 (m, 10H), 1.19 (d, 3H), 0.85 (dd, 1H), 0.59 (dd, 1H); $^{13}$C NMR (DMSO-$d_6$, 100 MHz) δ 174.2, 169.8, 48.6, 48.0, 37.0, 28.3, 26.9, 25.9, 25.4, 25.3, 18.6, 18.1; MS m/z 225 $(M+H)^+$.

Example 6

(1S)-spiro[2.5]octane-1-carboxylic acid

The product from Example 4 (25.0 0.112 mol, 97% diastereomeric excess), 1,4-dioxane (50 mL), and 4M $H_2SO_4$ (100 mL) were refluxed for 8 hours. The resulting solution was extracted with heptane (3×150 mL). The combined organic extracts were concentrated to afford the title compound (97% enantiomeric excess). The enantiomeric excess of the carboxylic acid was determined by chiral gas chromatography (GC) performed on a Hewlett-Packard 5890 Series gas chromatograph with a flame ionization detector (250° C.), and split mode capillary injection system (ratio 30:1), using a Chiraldex GTA column (30 m×0.25 mm, lot 06847 Serial # G0112-15); 1.0 μL injection volume, 250° C. injection temperature, helium carrier gas at 20 psi, oven temperature 160° C. isothermal, retention time of 9.02 minutes.

Example 7

(1S)-spiro[2.5]octane-1-carboxamide

The title compound can be prepared by using the procedure described in Example 2 substituting the product from Example 6 for the product from Example 1B.

Example 8

(1S)—N-(2-amino-2-oxoethyl)spiro[2.5]octane-1-carboxamide

The title compound was prepared by using the procedure described in Example 3 substituting the product from Example 6 for the product from Example 1B. The chiral purity was assessed by chiral HPLC: Chiral Pak AS, 4.6×250 mm; detector λ=210 nm, flow rate 1 mL/minute, eluted with 20% EtOH/hexane; retention time of 6.65 minutes. $^1$H NMR ($CH_3OD$, 300 MHz): δ 3.85 (dd, 2H), 1.2-1.6 (m, 10H), 1.05 (dd, 1H), 0.75 (dd, 1H); $^{13}$C NMR ($CH_3OD$, 100 MHz) δ 174.1, 173.9, 43.4, 38.6, 30.6, 28.8, 27.4, 26.8, 26.8, 19.7; MS m/z 211 $(M+H)^+$.

Example 9

(1R)-spiro[2.5]octane-1-carboxylic acid

The title compound was prepared by using the procedure described in Example 6 substituting the product from Example 5 for the product from Example 4. The enantiomeric excess of 97% was determined by chiral gas chromatography performed on a Hewlett-Packard 5890 Series gas chromatograph with a flame ionization detector (250° C.), and split mode capillary injection system (ratio 30:1), using a Chiraldex GTA column (30 m×0.25 mm, lot 06847 Serial # G0112-15); 1.0 μL injection volume, 250° C. injection temperature, helium carrier gas at 20 psi, oven temperature 160° C. isothermal, retention time 9.67 minutes.

Example 10

(1R)-spiro[2.5]octane-1-carboxamide

The title compound can be prepared by using the procedure described in Example 2 substituting the product from Example 9 for the product from Example 1B.

Example 11

(1R)—N-(2-amino-2-oxoethyl)spiro[2.5]octane-1-carboxamide

The title compound was prepared by using the procedure described in Example 3 substituting the product from Example 9 for the product from Example 1B. $^1$H NMR ($CH_3OD$, 400 MHz): δ 3.85 (m, 2H), 1.2-1.6 (m, 10H), 1.05 (dd, 1H), 0.75 (dd, 1H); $^{13}$C NMR ($CH_3OD$, 100 MHz) δ 174.1, 173.9, 43.4, 38.6, 30.6, 28.8, 27.4, 26.8, 26.8, 19.7; MS m/z 211 $(M+H)^+$. Chiral purity was determined by using the chiral HPLC conditions described in Example 8, retention time 8.04 minutes. $^1$H NMR ($CH_3OD$, 400 MHz): δ 3.85 (m, 2H), 1.2-1.6 (m, 10H), 1.05 (dd, 1H), 0.75 (dd, 1H); $^{13}$C NMR ($CH_3OD$, 100 MHz) δ 174.1, 173.9, 43.4, 38.6, 30.6, 28.8, 27.4, 26.8, 26.8, 19.7; MS m/z 211 $(M+H)^+$.

Example 12

Spiro[2.4]heptane-1-carboxylic acid

Example 12A

Ethyl spiro[2.4]heptane-1-carboxylate

The title compound was prepared as described in Example 1A substituting methylenecyclopentane (purchased from Aldrich) for methylenecyclohexane.

Example 12B

Spiro[2.4]heptane-1-carboxylic acid

The title compound was prepared as described in Example 1B substituting the product from Example 12A for the product from Example 1A.

Example 13

Spiro[2.4]heptane-1-carboxamide

The title compound was prepared as described in Example 2 substituting the product from Example 12B for the product from Example 1B. $^1$H NMR (DMSO-$d_6$, 300 MHz) δ 7.38 (s, 1H, $NH_2$), 6.71 (s, 1H, $NH_2$), 1.4-1.7 (m, 9H), 0.96 (dd, 1H), 0.79 (dd, 1H); $^{13}$C NMR (DMSO-$d_6$, 100 MHz) δ 172.8, 36.6, 31.0, 29.7, 27.2, 25.8, 25.5, 18.4.

Example 14

N-(2-amino-2-oxoethyl)spiro[2.4]heptane-1-carboxamide

The title compound was prepared as described in Example 3 substituting the product from Example 12B for the product from Example 1B. $^1$H NMR (DMSO-$d_6$, 300 MHz) δ 8.05 (t, 1H, NH), 7.28 (s, 1H, NH$_2$), 6.98 (s, 1H, NH$_2$), 3.62 (q, 2H, CH$_2$), 1.69 (dd, 1H), 1.3-1.7 (m, 8H), 0.99 (dd, 1H), 0.72 (dd, 1H); $^{13}$C NMR (DMSO-$d_6$, 100 MHz) δ 171.2, 171.2, 36.5, 31.2, 29.9, 27.3, 25.9, 25.5, 18.8; MS m/z 197 (M+H)$^+$.

Example 15

(1R,5S)-6,6-dimethylspiro[bicyclo[3.1.1]heptane-2,1'-cyclopropane]-2'-carboxylic acid

Example 15A

Ethyl (1R,5S)-6,6-dimethylspiro[bicyclo[3.1.1]heptane-2,1'-cyclopropane]-2'-carboxylate The title compound was prepared as described in Example 1A substituting (1S,5S)-6,6-dimethyl-2-methylenebicyclo[3.1.1]heptane (purchased from Aldrich) for methylenecyclohexane.

Example 15B (1R,5S)-6,6-dimethylspiro[bicyclo[3.1.1]heptane-2,1'-cyclopropane]-2'-carboxylic acid The title compound was prepared as described in Example 1B substituting the product from Example 15A for the product from Example 1A. MS m/z 212 (M+NH$_4$)$^+$.

Example 16

(1R,5S)-6,6-dimethylspiro[bicyclo[3.1.1]heptane-2,1'-cyclopropane]-2'-carboxamide The title compound was prepared as described in Example 2 substituting the product from Example 15B for the product from Example 1B. MS m/z 194 (M+H)$^+$.

Example 17

(1R,5S)—N-(2-amino-2-oxoethyl)-6,6-dimethylspiro[bicyclo[3.1.1]heptane-2,1'-cyclopropane]-2'-carboxamide The title compound was prepared as described in Example 3 substituting the product from Example 15B for the product from Example 1B. MS m/z 251 (M+H)$^+$.

Example 18

2-methylspiro[2.5]octane-1-carboxylic acid

Example 18A

Ethyl 2-methylspiro[2.5]octane-1-carboxylate

The title compound was prepared as described in Example 1A substituting ethylidenecyclohexane (purchased from Aldrich) for methylenecyclohexane.

Example 18B 2-methylspiro[2.5]octane-1-carboxylic acid

The title compound was prepared as described in Example 1B substituting the product from Example 18A for the product from Example 1A. MS m/z 186 (M+NH$_4$)$^+$.

Example 19

2-methylspiro[2.5]octane-1-carboxamide

The title compound was prepared as described in Example 2 substituting the product from Example 18B for the product from Example 1B.

Example 20

N-(2-amino-2-oxoethyl)-2-methylspiro[2.5]octane-1-carboxamide

The title compound was prepared as described in Example 3 substituting the product from Example 18B for the product from Example 1B. MS m/z 225 (M+H)$^+$.

Example 21

5,7-dimethylspiro[2.5]octane-1-carboxylic acid

Example 21A 1,3-dimethyl-5-methylenecyclohexane

The title compound was prepared as described in Example 45A substituting 3,5-dimethylcyclohexanone, commercially available from Aldrich, for 2-decalone.

Example 21B

Ethyl 5,7-dimethylspiro[2.5]octane-1-carboxylate

The title compound was prepared as described in Example 1A substituting the product from Example 21A for methylenecyclohexane.

Example 21C 5,7-dimethylspiro[2.5]octane-1-carboxylic acid

The title compound was prepared as described in Example 1B substituting the product from Example 21B for the product from Example 1A. MS m/z 182 (M+NH$_4$)$^+$.

Example 22

5,7-dimethylspiro[2.5]octane-1-carboxamide

The title compound can be prepared as described in Example 2 substituting the product from Example 21C for the product from Example 1B.

Example 23

N-(2-amino-2-oxoethyl)-5,7-dimethylspiro[2.5]oc-
tane-1-carboxamide

The title compound was prepared as described in Example 3 substituting the product from Example 21C for the product from Example 1B. MS m/z 239 (M+H)$^+$.

Example 24

6-tert-butylspiro[2.5]octane-1-carboxylic acid

Example 24A 1-tert-butyl-4-methylenecyclohexane

The title compound was prepared as described in Example 45A substituting 4-tert-Butyl cyclohexanone, commercially available from Aldrich, for 2-decalone.

Example 24B

Ethyl 6-tert-butylspiro[2.5]octane-1-carboxylate

The title compound was prepared as described in Example 1A substituting the product from Example 24A for methylenecyclohexane.

Example 24C 6-tert-butylspiro[2.5]octane-1-carboxylic acid

The title compound was prepared as described in Example 1B substituting the product from Example 24B for the product from Example 1A. MS m/z 228 (M+NH$_4$)$^+$.

Example 25

6-tert-butylspiro[2.5]octane-1-carboxamide

The title compound can be prepared as described in Example 2 substituting the product from Example 24C for the product from Example 1B.

Example 26

N-(2-amino-2-oxoethyl)-6-tert-butylspiro[2.5]oc-
tane-1-carboxamide

The title compound can be prepared as described in Example 3 substituting the product from Example 24C for the product from Example 1B. MS m/z 228 (M+NH$_4$)$^+$.

Example 27

2-methylspiro[2.4]heptane-1-carboxylic acid

Example 27A

Ethyl 2-methylspiro[2.4]heptane-1-carboxylate

The title compound was prepared as described in Example 1A substituting ethylenecyclopentane, purchased from Avocado, for methylenecyclohexane.

Example 27B 2-methylspiro[2.4]heptane-1-carboxylic acid

The title compound was prepared as described in Example 1B substituting the product from Example 27A for the product from Example 1A. MS m/z 154 (M)$^+$.

Example 28

2-methylspiro[2.4]heptane-1-carboxamide

The title compound was prepared as described in Example 2 substituting the product from Example 27B for the product from Example 1B. MS m/z 154 (M+H)$^+$.

Example 29

N-(2-amino-2-oxoethyl)-2-methylspiro[2.4]heptane-
1-carboxamide

The title compound was prepared as described in Example 3 substituting the product from Example 27B for the product from Example 1B. MS m/z 211 (M+H)$^+$.

Example 30

3,3-dimethylspiro[bicyclo[2.2.1]heptane-2,1'-cyclo-
propane]-2'-carboxylic acid

Example 30A

Ethyl 3,3-dimethylspiro[bicyclo[2.2.1]heptane-2,1'-
cyclopropane]-2'-carboxylate The title compound was prepared as described in Example 1A substituting 2,2-dimethyl-3-methylenebicyclo[2.2.1] heptane, purchased from Aldrich, for methylenecyclohexane.

Example 30B 3,3-dimethylspiro[bicyclo[2.2.1]heptane-2,1'-cyclo-
propane]-2'-carboxylic acid The title compound was prepared as described in Example 1B substituting the product from Example 30A for the product from Example 1A. MS m/z 194 (M)$^+$.

Example 31

3,3-dimethylspiro[bicyclo[2.2.1]heptane-2,1'-cyclo-
propane]-2'-carboxamide

The title compound was prepared as described in Example 2 substituting the product from Example 30B for the product from Example 1B.

Example 32

N-(2-amino-2-oxoethyl)-3,3-dimethylspiro[bicyclo
[2.2.1]heptane-2,1'-cyclopropane]-2'-carboxamide The title compound was prepared as described in Example 3 substituting the product from Example 30B for the product from Example 1B. MS (APCI) m/z 251 (M+H)$^+$.

Example 33

4-methylspiro[bicyclo[3.2.0]heptane-6,1'-cyclopropane]-2'-carboxylic acid 2-methyl-7-methylenebicyclo[3.2.0]heptane The title compound was prepared as described in Example 45A substituting 4-methylbicyclo[3.2.0]hept-6-one, prepared as described in Dowd, Paul; Zhang, Wei., J. Am. Chem. Soc. (1992), 114, 10084-5, for 2-decalone.

Example 33B

Ethyl 4-methylspiro[bicyclo[3.2.0]heptane-6,1'-cyclopropane]-2'-carboxylate

The title compound was prepared as described in Example 1A substituting the product from Example 33A for methylenecyclohexane.

Example 33C 4-methylspiro[bicyclo[3.2.0]heptane-6,1'-cyclopropane]-2'-carboxylic acid The title compound was prepared as described in Example 1B substituting the product from Example 33B for the product from Example 1A. MS (ESI) m/z 179 (M–H)⁻.

Example 34

4-methylspiro[bicyclo[3.2.0]heptane-6,1'-cyclopropane]-2'-carboxamide

The title compound was prepared as described in Example 2 substituting the product from Example 33C for the product from Example 1B. MS (APCI) m/z 180 (M+H)⁺.

Example 35

N-(2-amino-2-oxoethyl)-4-methylspiro[bicyclo[3.2.0]heptane-6,1'-cyclopropane]-2'-carboxamide The title compound was prepared as described in Example 3 substituting the product from Example 33C for the product from Example 1B. MS (APCI) m/z 237 (M+H)⁺.

Example 36

Spiro[bicyclo[2.2.1]heptane-2,1'-cyclopropane]-2'-carboxylic acid

Example 36A 2-methylenebicyclo[2.2.1]heptane

The title compound was prepared as described in Example 45A substituting bicyclo[2.2.1]heptan-2-one, purchased from Aldrich, for 2-decalone.

Example 36B

Ethyl spiro[bicyclo[2.2.1]heptane-2,1'-cyclopropane]-2'-carboxylate

The title compound was prepared as described in Example 1A substituting the product from Example 36A for methylenecyclohexane.

Example 36C

Spiro[bicyclo[2.2.1]heptane-2,1'-cyclopropane]-2'-carboxylic acid

The title compound was prepared as described in Example 1B substituting the product from Example 36B for the product from Example 1A. MS (ESI) m/z 165 (M–H)⁻.

Example 37

Spiro[bicyclo[2.2.1]heptane-2,1'-cyclopropane]-2'-carboxamide

The title compound was prepared as described in Example 2 substituting the product from Example 36C for the product from Example 1B. MS (APCI) m/z 166 (M+H)⁺.

Example 38

N-(2-amino-2-oxoethyl)spiro[bicyclo[2.2.1]heptane-2,1'-cyclopropane]-2'-carboxamide The title compound was prepared as described in Example 3 substituting the product from Example 36C for the product from Example 1B. MS (APCI) m/z 223 (M+H)⁺.

Example 39

Spiro[2.6]nonane-1-carboxylic acid

Example 39A

Methylenecycloheptane

The title compound was prepared as described in Example 45A substituting cycloheptanone, purchased from Aldrich, for 2-decalone.

Example 39B

Ethyl spiro[2.6]nonane-1-carboxylate

The title compound was prepared as described in Example 1A substituting the product from Example 39A for methylenecyclohexane.

Example 39C

Spiro[2.6]nonane-1-carboxylic acid

The title compound was prepared as described in Example 1B substituting the product from Example 39B for the product from Example 1A. $^{13}$C NMR (CDCl$_3$, 100 MHz) δ 23.7, 26.2, 26.4, 27.2, 27.9, 28.0, 28.4, 31.2, 33.4, 33.5, 40.1, 179.3; MS m/z 168 (M)⁺.

Example 40

Spiro[2.6]nonane-1-carboxamide

The title compound was prepared as described in Example 2 substituting the product from Example 39C for the product from Example 1B. $^1$H NMR (CDCl$_3$, 300 MHz) δ 0.78 (dd, 1H), 1.12 (t, 1H), 1.34 (dd, 1H), 1.41-1.62 (m, 10H), 1.68-1.72 (m, 2H), 5.68-5.75 (br m, 2H); $^{13}$C NMR (CDCl$_3$, 100 MHz) δ 21.4, 26.2, 26.5, 28.1, 28.1, 29.0, 31.0, 31.2, 40.1, 173.8; MS m/z 168 (M+H)$^+$.

Example 41

N-(2-amino-2-oxoethyl)spiro[2.6]nonane-1-carboxamide

The title compound was prepared as described in Example 3 substituting the product from Example 39C for the product from Example 1B. $^1$H NMR (CDCl$_3$, 300 MHz) δ 0.78 (d), 0.80 (d), 1.11 (t), 1.39-1.57 (m), 1.65 (t), 3.91-4.03 (m), 5.91 (br s), 6.75 (br s), 6.88 (t); $^{13}$C NMR (CDCl$_3$, 100 MHz) δ 21.3, 26.3, 26.5, 28.0, 28.1, 29.2, 31.1, 31.3, 40.1, 43.3, 171.7, 172.3; MS m/z 225 (M+H)$^+$.

Example 42

(4S,7R)-4-isopropyl-7-methylspiro[2.5]octane-1-carboxylic acid

Example 42A (1S,4R)-1-isopropyl-4-methyl-2-methylenecyclohexane

The title compound was prepared as described in Example 45A substituting (2S,5R)-2-isopropyl-5-methylcyclohexanone, purchased from Aldrich, for 2-decalone.

Example 42B

Ethyl (4S,7R)-4-isopropyl-7-methylspiro[2.5]octane-1-carboxylate

The title compound was prepared as described in Example 1A substituting the product from Example 42A for methylenecyclohexane.

Example 42C (4S,7R)-4-isopropyl-7-methylspiro[2.5]octane-1-carboxylic acid

The title compound was prepared as described in Example 1B substituting the product from Example 42B for the product from Example 1A. MS m/z 210 (M)$^+$.

Example 43

(4S,7R)-4-isopropyl-7-methylspiro[2.5]octane-1-carboxamide

The title compound was prepared as described in Example 2 substituting the product from Example 42C for the product from Example 1B. MS m/z 210 (M+H)$^+$.

Example 44

(4S,7R)—N-(2-amino-2-oxoethyl)-4-isopropyl-7-methylspiro[2.5]octane-1-carboxamide The title compound was prepared as described in Example 3 substituting the product from Example 42C for the product from Example 1B. MS m/z 267 (M+H)$^+$.

Example 45

Octahydro-1'H-spiro[cyclopropane-1,2'-naphthalene]-2-carboxylic acid

Example 45A 2-methylenedecahydronaphthalene

To a stirred slurry of potassium tert-butoxide (30.9 g, 0.276 mol, purchased from Aldrich) in tert-butyl methyl ether (200 mL) under nitrogen was added methyltriphenylphosphonium bromide (98.6 g, 0.276 mol, purchased from Aldrich). The resultant yellow mixture was heated at 45° C. for 1 hour then 2-decalone (40.0 g, 0.263 mol, purchased from Aldrich) was added dropwise over 1 hour. The mixture was heated at 60° C. for 18 hours then cooled to ambient temperature and quenched with water (400 mL). The organic extract was concentrated to provide an oily residue that was diluted with pentane (2×160 mL) causing formation of a precipitate (triphenylphoshine oxide) that was removed by filtration. The filtrate was washed with water (100 mL) and concentrated to provide an oil (37.7 g) that was purified by vacuum distillation (house vacuum, vessel warmed to 110° C.) to afford the title compound as a colorless oil (32.1 g, 81.3% yield) that was analytically pure by HPLC and $^1$H NMR. HPLC conditions: Zorbax Rx-C8, 5 μm, 4.6×250 mm, 10:90 to 90:10 MeCN:0.1% aqueous H$_3$PO$_4$ gradient from 0-15 minutes then 90:10 MeCN:0.1% aqueous H$_3$PO$_4$ for 5 minutes, wavelength 200 nm, flow rate 1.5 mL/min, ambient temperature, retention time for title compound: 16.45 minutes; $^1$H NMR (CDCl$_3$, 400 MHz) δ 0.83-1.16 (m 1H), 1.20-1.82 (m, 11H), 1.88-2.37 (m, 4), 4.52-4.61 (m, 2H); MS m/z (DCI) 170 (M+NH$_4$)$^+$.

Example 45B

Ethyl octahydro-1'H-spiro[cyclopropane-1,2'-naphthalene]-2-carboxylate

The title compound was prepared as described in Example 1A substituting the product from Example 45A for methylenecyclohexane.

Example 45C

Octahydro-1'H-spiro[cyclopropane-1,2'-naphthalene]-2-carboxylic acid

The title compound was prepared as described in Example 1B substituting the product from Example 45B for the product from Example 1A. MS m/z 208 (M)$^+$.

Example 46

Octahydro-1'H-spiro[cyclopropane-1,2'-naphthalene]-2-carboxamide

The title compound was prepared as described in Example 2 substituting the product from Example 45C for the product from Example 1B. MS m/z 208 (M+H)$^+$.

Example 47

N-(2-amino-2-oxoethyl)octahydro-1'H-spiro[cyclopropane-1,2'-naphthalene]-2-carboxamide The title compound was prepared as described in Example 3 substituting the product from Example 45C for the product from Example 1B. MS m/z 265 (M+H)$^+$.

Example 48

N-(3-amino-3-oxopropyl)spiro[2.5]octane-1-carboxamide

The title compound was prepared as described in Example 3 substituting 3-aminopropanamide for 2-aminoacetamide. $^1$H NMR (CD$_3$OD, 400 MHz) δ 3.44 (t, 2H), 2.40 (t, 2H), 1.2-1.6 (m, 10H), 1.02 (dd, 1H), 0.63 (dd 1H); $^{13}$C NMR (CD$_3$OD, 100 MHz) δ 175.9, 173.7, 38.6, 37.1, 36.4, 30.2, 30.1, 28.9, 27.4, 26.9, 26.8, 19.2; MS m/z 225 (M+H)$^+$.

Example 49

Spiro[2.7]decane-1-carboxylic acid

Example 49A

Methylenecyclooctane

The title compound was prepared as described in Example 21A substituting cyclooctanone for 3,5-dimethylcyclohexanone.

Example 49B

Ethyl spiro[2.7]decane-1-carboxylate

The title compound was prepared as described in Example 1A substituting the product from Example 49A for methylenecyclohexane.

Example 49C

Spiro[2.7]decane-1-carboxylic acid

The title compound was prepared as described in Example 1B substituting the product from Example 49B for the product from Example 1A.

Example 50

Spiro[2.7]decane-1-carboxamide

The title compound can be prepared as described in Example 2 substituting the product from Example 49C for the product from Example 1B.

Example 51

N-(2-amino-2-oxoethyl)spiro[2.7]decane-1-carboxamide

The title compound was prepared as described in Example 3 substituting the product from Example 49C for the product from Example 1B.

Example 52

5,5,7,7-tetramethylspiro[2.5]octane-1-carboxylic acid

Example 52A 1,1,3,3-tetramethyl-5-methylenecyclohexane

The title compound was prepared as described in Example 45A substituting 3,3,5,5-tetramethylcyclohexanone (purchased from Wiley) for 2-decalone.

Example 52B

Ethyl 5,5,7,7-tetramethylspiro[2.5]octane-1-carboxylate

The title compound was prepared as described in Example 1A substituting the product from Example 52A for methylenecyclohexane.

Example 52C 5,5,7,7-tetramethylspiro[2.5]octane-1-carboxylic acid

The title compound was prepared as described in Example 1B substituting the product from Example 52B for the product from Example 1A. $^1$H NMR (DMSO-d$_6$, 300 MHz) δ 1.34-1.43 (m, 3H), 1.11-1.19 (m, 4H), 0.95 (s, 3H), 0.93 (s, 3H), 0.92 (s, 3H), 0.87 (m, 1H), 0.85 (s, 3H), 0.82 (dd, J=4.0, 7.9 Hz, 1H); $^{13}$C NMR (DMSO-d$_6$, 100 MHz) δ 19.3, 24.9, 25.7, 30.7, 30.9, 31.2, 31.5, 32.0, 32.4, 40.1, 48.7, 51.9, 173.2.

Example 53

5,5,7,7-tetramethylspiro[2.5]octane-1-carboxamide

The title compound was prepared as described in Example 2 substituting the product from Example 52C for the product from Example 1B. $^1$H NMR (DMSO-d$_6$, 300 MHz) δ 7.40 (br s, 1H), 6.64 (br s, 1H), 1.38-1.41 (m, 3H), 1.08-1.22 (m, 3H), 1.03 (m, 1H), 0.94 (s, 6H), 0.92 (s, 3H), 0.88 (m, 1H), 0.83 (s, 3H), 0.67 (dd, J=3.7, 7.9 Hz, 1H); $^{13}$C NMR (DMSO-d$_6$, 100 MHz) δ 18.2, 24.2, 25.4, 30.6, 30.7, 31.8, 31.9, 32.4, 39.9, 49.2, 52.2, 172.5; MS (APCI) m/z 210 (M+H)$^+$.

Example 54

N-(2-amino-2-oxoethyl)-5,5,7,7-tetramethylspiro[2.5]octane-1-carboxamide

The title compound was prepared as described in Example 3 substituting the product from Example 52C for the product from Example 1B. $^1$H NMR (DMSO-d$_6$, 300 MHz) δ 8.07 (br t, J=5.7 Hz, 1H), 7.21 (br s, 1H), 6.95 (br s, 1H), 0.95-1.45 (m, 8H), 0.94 (s, 3H), 0.93 (s, 3H), 0.92 (s, 3H), 0.79 (s, 3H), 0.71

(m, 1H); $^{13}$C NMR (DMSO-d$_6$, 100 MHz) δ 18.5, 24.4, 25.5, 30.5, 30.6, 31.7, 32.0, 32.1, 32.4, 39.9, 41.1, 49.0, 52.1, 170.7, 170.9; MS m/z (APCI) 267 (M+H)$^+$.

Example 55

[(spiro[2.5]oct-1-ylcarbonyl)amino]acetic acid

The product from Example 1B (4.50 g, 29.2 mmol), and 1,1'-carbonyldiimidazole (5.0 g, 30.8 mmol, 1.06 equiv) were combined in 1,2-dimethoxyethane (50 mL) and stirred at room temperature for 1.5 hours. Glycine methyl ester hydrochloride (3.85 g, 30.8 mmol, 1.06 equiv, purchased from Aldrich) and water (0.2 mL) were added and the reaction mixture was heated at 65° C. for 6 hours. The reaction solution was cooled to room temperature, diluted with ethyl acetate (250 mL) and washed water (2×100 mL). The organic extract was concentrated and the residue was dissolved in ethanol (20 mL). An aqueous solution of NaOH (1.52 g, 38 mmol, 1.3 equiv) was added and the mixture was agitated at room temperature for 1 hour. The reaction mixture was diluted with ethyl acetate (250 mL) and water (100 mL), which was acidified with to pH 3 by the addition of concentrated HCl. The organic extract was concentrated and the residue was crystallized from ethyl acetate (40 mL) to afford the title compound (4.0 g, 65%). $^1$H NMR (CDCl$_3$, 400 MHz) δ 6.30 (m, 1H), 4.10 (d, 2H), 1.25-1.7 (m, 11H), 1.16 (dd, 1H), 0.81 (dd, 1H); MS, m/z, 212 (M+H)$^+$.

Example 56

{[(1S)-spiro[2.5]oct-1-ylcarbonyl]amino}acetic acid

The product from Example 6 (15.4 g, 0.100 mol) and 1,1'-carbonyldiimidazole (17.8 g, 0.110 mol) were combined in ethyl acetate (250 mL) and stirred at room temperature for 1.5 hours. Glycine methyl ester hydrochloride (12.67 g, 0.100 mol, purchased from Aldrich) and water (10 mL) were added and the reaction mixture was refluxed for 3 hours. The reaction solution was cooled to room temperature and diluted with 1 N aqueous HCl. The layers were separated and aqueous phase was extracted with ethyl acetate (100 mL). The combined organic extracts were concentrated. The residue was dissolved in 1:1 MeOH/water (200 mL) and LiOH monohydrate (15 g, 0.357 mol) was added. The resulting solution was refluxed for 15 minutes, cooled to room temperature and then extracted twice with heptane (150 mL). The aqueous phase was acidified to pH 2 by the addition of 5 M aqueous H$_2$SO$_4$ and extracted with ethyl acetate (3×250 mL). The EtOAc extracts were combined, dried over MgSO$_4$, filtered and concentrated. The residue was crystallized from ethyl acetate (150 mL) to afford the title compound (9.5 g, 45%). $^1$H NMR (CDCl$_3$, 400 MHz), δ 10.72 (br s, 1H), 6.47 (t, 1H), 4.07 (d, 2H), 1.25-1.70 (m, 11H), 1.13 (dd, 1H), 0.78 (dd, 1H); MS, m/z, 212 (M+H)$^+$; $^{13}$C NMR (DMSO-d$_6$, 100 MHz) δ 19.7, 25.8, 26.0, 26.4, 28.1, 29.0, 30.6, 37.7, 42.1, 172.5, 172.6; MS m/z (DCI) 212 (M+H)$^+$, 229 (M+NH$_4$)$^+$.

Example 57

{[(1R)-spiro[2.5]oct-1-ylcarbonyl]amino}acetic acid

The title compound was prepared in 89% yield by using the procedure described in Example 52 substituting the product from Example 9 (5.92 g, 38.4 mmol) for the product from Example 6. $^1$H NMR (CD$_3$OD, 400 MHz), δ 4.89 (m, 2H), 1.25-1.70 (m, 11H), 1.03 (dd, 1H), 0.73 (dd, 1H); $^{13}$C NMR (CD$_3$OD, 100 MHz), δ 174.0, 172.5, 42.0, 38.7, 30.6, 30.0, 28.8, 27.4, 26.8, 26.7 and 19.6; MS (DCI) m/z 212 (M+H)$^+$.

Example 58

Spiro[bicyclo[3.2.0]heptane-6,1'-cyclopropane]-2'-carboxylic acid

Example 58A 6-methylenebicyclo[3.2.0]heptane

The title compound was prepared as described in Example 45A substituting bicyclo[3.2.0]heptan-6-one, prepared as described in Marko, Istvan; et. al., J. Am. Chem. Soc. (1985), 107(7), 2192-4.) for 2-decalone.

Example 58B

Ethyl spiro[bicyclo[3.2.0]heptane-6,1'-cyclopropane]-2'-carboxylate

The title compound was prepared as described in Example 1A substituting the product from Example 58A for methylenecyclohexane.

Example 58C

Spiro[bicyclo[3.2.0]heptane-6,1'-cyclopropane]-2'-carboxylic acid

The title compound was prepared as described in Example 1B substituting the product from Example 58B for the product from Example 1A. MS (CI) m/z 67 (M+H)$^+$.

Example 59

Spiro[bicyclo[3.2.0]heptane-6,1'-cyclopropane]-2'-carboxamide

The title compound can be prepared as described in Example 2 substituting the product from Example 58C for the product from Example 1B.

Example 60

N-(2-amino-2-oxoethyl)spiro[bicyclo[3.2.0]heptane-6,1'-cyclopropane]-2'-carboxamide The title compound was prepared as described in Example 3 substituting the product from Example 58C for the product from Example 1B. MS (APCI) m/z 223 (M+H)$^+$.

Example 61

(1R)—N-[(2R)-2-hydroxypropyl]spiro[2.5]octane-1-carboxamide

The title compound was prepared as described in Example 3 substituting the product from Example 9 for the product from Example 1B and substituting (R)-1-amino-2-propanol, purchased from Aldrich, for 2-aminoacetamide hydrochloride. $^1$H NMR (400 MHz, CD$_3$OD) δ 3.80 (m, 1H), 3.16 (m, 2H), 1.20-1.70 (m, 11H), 1.13 (d, 3H), 1.02 (dd, 1H), 0.69 (dd, 1H); $^{13}$C NMR (DMSO-d$_6$, 100 MHz) δ 173.9, 67.5, 48.0, 38.7, 30.2, 30.0, 28.9, 27.5, 26.9, 26.8, 21.1, 19.4; MS (CI) m/z 212 (M+H)$^+$.

Example 62

(1S)—N-[(2R)-2-hydroxypropyl]spiro[2.5]octane-1-carboxamide

The title compound was prepared as described in Example 3 substituting the product from Example 6 for the product from Example 1B and substituting (R)-1-amino-2-propanol, purchased from Aldrich, for 2-aminoacetamide hydrochloride. $^1$H NMR (400 MHz, CD$_3$OD) δ 3.80 (m, 1H), 3.16 (m, 2H), 1.20-1.70 (m, 11H), 1.13 (d, 3H), 1.02 (dd, 1H), 0.69 (dd, 1H); $^{13}$C NMR (DMSO-d$_6$, 100 MHz) δ 173.9, 67.5, 48.0, 38.7, 30.2, 30.0, 28.9, 27.5, 26.9, 26.8, 21.1, 19.4; MS (CI) m/z 212 (M+H)$^+$.

Example 63

(1R)—N-[(2S)-2-hydroxypropyl]spiro[2.5]octane-1-carboxamide

The title compound was prepared as described in Example 3 substituting the product from Example 9 for the product from Example 1B and substituting (S)-1-amino-2-propanol, purchased from Aldrich, for 2-aminoacetamide hydrochloride. $^1$H NMR (400 MHz, CD$_3$OD) δ 3.80 (m, 1H), 3.16 (m, 2H), 1.20-1.70 (m, 11H), 1.13 (d, 3H), 1.02 (dd, 1H), 0.69 (dd, 1H); MS (CI) m/z 212 (M+H)$^+$.

Example 64

(1S)—N-[(2S)-2-hydroxypropyl]spiro[2.5]octane-1-carboxamide

The title compound was prepared as described in Example 3 substituting the product from Example 6 for the product from Example 1B and substituting (S)-1-amino-2-propanol, purchased from Aldrich, for 2-aminoacetamide hydrochloride. $^1$H NMR (400 MHz, CD$_3$OD) δ 3.80 (m, 1H), 3.16 (m, 2H), 1.20-1.70 (m, 11H), 1.13 (d, 3H), 1.02 (dd, 1H), 0.69 (dd, 1H); MS (CI) m/z 212 (M+H)$^+$.

Example 65

(1R)—N-methylspiro[2.5]octane-1-carboxamide

The title compound can be prepared by using the procedure described in Example 2 except replacing the product from Example 1B with the product from Example 9 and replacing ammonium hydroxide with N-methylamine.

Example 66

(1S)—N-methylspiro[2.5]octane-1-carboxamide

The title compound can be prepared by using the procedure described in Example 2 except replacing the product from Example 1B with the product from Example 6 and replacing ammonium hydroxide with N-methylamine.

Determination of Anticonvulsant Effect

The anticonvulsant effect of a representative number of compounds of the present invention were determined using the procedures described hereinafter.

Adult, male, CD-1 mice (22-25 grams) were obtained from Charles River Laboratories (Portage, Mich.) and housed at Abbott Laboratories (Abbott Park) under standard lighting conditions of 12 hours on/12 hours off, with lights on at 6 a.m. Food and water were provided ad libitum and mice weighed 25-35 grams at the time of testing.

Compounds were prepared for oral administration by suspending them in a vehicle of 100 µL Tween® 80 per mL hydroxypropyl methylcellulose (2 mg/mL, Abbott Laboratories). Compound solutions were administered at a volume of 10 mL/kg, p.o.

Maximal Electroshock Procedure:

The method used was similar to that of E. A. Swinyard, General principles: Experimental selection, quantification and evaluation of anti-convulsants, Anti-epileptic Drugs, Third Edition, R. Levey, et al., Editors. 1989, Raven Press Ltd: New York. Mice were pretreated orally with compounds of the present invention 30 minutes prior to electrical stimulation. Electrical stimulation consisted of pulsed electrical current (50 mA, 0.4 second duration, pulse width 0.5 msec, 60 pulses/sec) applied via corneal electrodes to induce seizure. The stimulation was delivered with an ECT Unit (Ugo Basile #7801). The electrodes of the unit were coated with electrocardiogram electrolyte (Signa Creme, Parker Labs #1708) to insure good contact with the corneas. Mice were observed post-stimulation for the onset of tonic seizures and death. Mice were considered to have had a tonic seizure only if there was a prolonged extension (>90° from plane of body) of the hind legs. Mice were assigned scores of either "positive" or "negative." A positive score indicated that the symptom was present; a negative that it was not. Those that did not seize were considered protected. A total of 20 mice were used in each group. The percent protection from tonic seizures was calculated by dividing the number of protected mice by the total number in the group. The ED$_{50}$ for the compounds were calculated using PROBIT analysis and represent the dose at which 50% of the mice were protected from tonic seizures. Valproate exhibited an ED$_{50}$ of 1.2 mmol/kg. Representative compounds of the present invention exhibited ED$_{50s}$ in the range of about 0.36 mmol/kg to about 0.20 mmol/kg.

Subcutaneous Pentylenetetrazole (PTZ) Seizure Procedure:

The method used was similar to that of E. A. Swinyard, General principles: Experimental selection, quantification and evaluation of anti-convulsants, Anti-epileptic Drugs, Third Edition, R. Levey, et al., Editors. 1989, Raven Press Ltd: New York. During the experiment the mice were housed individually in clear polycarbonate cages for observation. Mice, excluding control, were pretreated orally with a compound of the present invention 30 minutes prior to PTZ injection and were observed for 15 minutes following administration of PTZ. Seizures were induced by the subcutaneous injection of pentylenetetrazole (PTZ, 85 mg/kg) just below the nape of the neck. Time to clonic and tonic seizures was noted, and the number of mice that exhibited seizures was recorded. A total of 20 mice were used in each group. The ED$_{50}$ for the compounds were calculated using linear regression and represent the dose at which 50% of the mice were protected from tonic seizures. Valproate exhibited an ED$_{50}$ of 1.8 mmol/kg. Representative compounds of the present invention exhibited ED$_{50}$ in the range of about 0.84 mmol/kg to about 0.35 mmol/kg.

Compounds of the present invention can be used to treat seizures including, but not limited to, epilepsy as described by Schmidt, D., The clinical impact of new antiepileptic drugs after a decade of use in epilepsy, Epilepsy Res., 2002, 50(1-2), 21-32; Asconape, J. J., Some common issues in the use of antiepileptic drugs, Seminars in Neurology, 2002, 22(1), 27-39; and Wallace, S. J., Newer antiepileptic drugs: advantages and disadvantages, Brain & Development, 2001, 23, 277-283.

Compounds of the present invention can be used to treat bipolar disorder as described by Brambilla, P., Barale, F., Soares, J. C., Perspectives on the use of anticonvulsants in the treatment of bipolar disorder, International Journal of Neuropsychopharmacology, 2001, 4, 421-446; Angel, I. and Horovitz, T., Bipolar disorder and valproic acid, Current Opinion in Central & Peripheral Nervous System Investigational Drugs (1999), 1(4), 466-469; Muzina, D. J., El-Sayegh, S., Calabrese, J. R., Antiepileptic drugs in psychiatry-focus on randomized controlled trial, Epilepsy Research, 2002, 50 (1-2), 195-202; and Calabrese, J. R., Shelton, M. D., Rapport, D. J., Kimmel, S. E., Bipolar disorders and the effectiveness of novel anticonvulsants, J. Clin. Psychiatry, 2002, 63 (suppl 3), 5-9.

Compounds of the present invention can be used to treat psychiatric disorders including, but not limited to, anxiety and panic disorders, post-traumatic stress disorder, schizophrenia, episodic dyscontrol, substance-abuse-related disorders, impulse control disorders, general agitation associated with a variety of psychiatric disorders and dementias, and behavioral disorders associated with autism as described in Bialer, M., Johannessen, S. I., Kupferberg, H. J., Levy, R. H., Loiseau, P., Perucca, E., Progress report on new antiepileptic drugs: a summary of the sixth eilat conference (EILAT VI), Epilepsy Res. 2002, 51, 31-71; Fountain, N. B., Dreifuss, F. E., The future of valproate. In: Valproate., Loscher W., Editor. 1999, Birkhauser Verlag, Boston; Fountain, N. B., Dreifuss, F. E., The future of valproate. In: Valproate., Löscher W., Editor. 1999, Birkhauser Verlag, Boston; and Balfour, J. A., Bryson, H. M. Valproic acid: A review of its pharmacology and therapeutic potential in indications other than epilepsy, CNS Drugs, 1994, 2 (2), 144-173.

Compounds of the present can be used to treat different types of migraine such as classical migraine and common migraine as described in Wheeler, S. D., Antiepileptic drugs therapy in migraine headache, Current Treatment Options in Neurology, 2002, 4, 383-394; and Krymchantowski, A. V., Bigal, M. E., Moreira, P. E., New and emerging prophylactic agents for migraine, CNS Drugs, 2002, 16 (9), 611-634.

Compounds of the present invention can be used to treat pain including, but not limited to, neuropathic pain including, but no limited to, diabetic neuropathy, cancer neuropathy, HIV pain, trigeminal neuralgia, post-herpetic neuralgia, traumatic neuralgia, phantom limb, severe refractory pain, and lancinating pain as described in Tremont-Lukats, I. W., Megeff, C., Backonja, M.-M., Anticonvulsants for neuropathich pain syndromes: mechanisms of action and place in therapy, Drugs, 60 (5), 1029-1052; Jensen, T. S., Anticonvulsants in neuropathic pain: rationale and clinical evidence, Eur. J. Pain, 2002, 6 (suppl A), 61-68; and Balfour, J. A., Bryson, H. M. Valproic acid: A review of its pharmacology and therapeutic potential in indications other than epilepsy, CNS Drugs, 1994, 2 (2), 144-173; Hardy, J. R., Rees, E. A. J., Gwilliam, B., Ling, J., Broadley, K., A'Hem, R., J. of Pain and Symptom Management, 2001, 21 (3), 204-209.

Compounds of the present invention can be used to provide neuroprotection as described in Pitkanen, A., Efficacy of current antiepileptics to prevent neurodegeneration in epilepsy models, Epilepsy Research, 2002, 50, 141-160.

Compounds of the present invention can be used to treat movement disorders including, but not limited to, restless leg syndrome, periodic limb movements of sleep, essential tremor, acquired nystagmus, post-anoxic myoclonus, spinal myoclonus, spasticity, chorea, and dystonia as described in Magnus, L., Nonepileptic uses of gabapentin, Epilepsia, 1999, 40 (suppl 6), S66-S72; Fountain, N. B., Dreifuss, F. E., The future of valproate. In: Valproate., Loscher W., Editor. 1999, Birkhauser Verlag, Boston; Cutter, N., Scott, D. D., Johnson, J. C., Whiteneck, G., Gabapentin effect on spacticity in multiple sclerosis, 2000, 81, 164-169.

The present invention also provides pharmaceutical compositions that comprise compounds of the present invention. The pharmaceutical compositions comprise compounds of the present invention formulated together with one or more non-toxic pharmaceutically acceptable carriers.

The pharmaceutical compositions of this invention can be administered to humans and other mammals orally, rectally, parenterally, intracisternally, intravaginally, topically (as by powders, ointments or drops), bucally or as an oral or nasal spray. The term "parenterally," as used herein, refers to modes of administration which include intravenous, intramuscular, intraperitoneal, intrasternal, subcutaneous and intraarticular injection and infusion.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable carrier or excipient, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated.

When used in the above or other treatments, a therapeutically effective amount of one of the compounds of the present invention can be employed in pure form or, where such forms exist, in pharmaceutically acceptable salt, ester or prodrug form. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The term "pharmaceutically acceptable prodrug" or "prodrug," as used herein, represents those prodrugs of the compounds of the present invention which are, within the scope of sound medical judgement, suitable for use in contact with the tissues of humans and lower animals without undue toxicity, irritation, allergic response, and the like. Prodrugs of the present invention may be rapidly transformed in vivo to compounds of formula (I), for example, by hydrolysis in blood.

The present invention contemplates compounds of formula (I) formed by synthetic means or formed by in vivo biotransformation.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

The total daily dose of the compounds of this invention administered to a human or lower animal may range from about 0.003 to about 90 mg/kg/day. For purposes of oral administration, more preferable doses can be in the range of from about 0.01 to about 30 mg/kg/day. If desired, the effective daily dose can be divided into multiple doses for purposes of administration; consequently, single dose compositions may contain such amounts or submultiples thereof to make up the daily dose.

What is claimed is:

1. A method of treating migraine, epilepsy, or bipolar disorder in a mammal comprising administering to a mammal a therapeutically effective amount of a compound of formula (I)

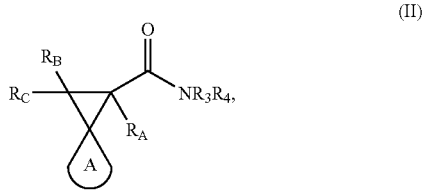

(II)

wherein
A is cyclohexyl optionally substituted with 1, 2, 3, or 4 alkyl groups;
$R_A$, $R_B$, and $R_C$ are independently hydrogen or alkyl;
$R_1$ is $OR_2$ or $NR_3R_4$;
$R_2$ is hydrogen;
$R_3$ and $R_4$ are independently hydrogen, carboxyalkyl, hydroxyalkyl, or $(NR_5R_6)$carbonylalkyl; and
$R_5$ and $R_6$ are hydrogen.

2. The method according to claim 1 wherein $R_1$ is $OR_2$.
3. The method according to claim 1 wherein $R_1$ is $OR_2$.
4. The method according to claim 3 wherein the compound of formula (I) is
spiro[2.5]octane-1-carboxylic acid;
(1S)-spiro[2.5]octane-1-carboxylic acid;
(1R)-spiro[2.5]octane-1-carboxylic acid;
2-methylspiro[2.5]octane-1-carboxylic acid;
5,7-dimethylspiro[2.5]octane-1-carboxylic acid;
6-tert-butylspiro[2.5]octane-1-carboxylic acid;
(4S3R)-4-isopropyl-7-methylspiro[2.5]octane-1-carboxylic acid; or
5,5,7,7-tetramethylspiro[2.5]octane-1-carboxylic acid.

5. The method according to claim 1 wherein
$R_1$ is $NR_3R_4$.
6. The method according to claim 1 wherein
$R_1$ is $NR_3R_4$;
$R_4$ is hydrogen or $(NR_5R_6)$carbonylalkyl; and
$R_3$ is hydrogen.
7. The method according to claim 6 wherein the compound of formula (I) is
spiro[2.5]octane-1-carboxamide;
N-(2-amino-2-oxoethyl)spiro[2.5]octane-1-carboxamide;
(1S)—N-[(1S)-2-amino-1-methyl-2-oxoethyl]spiro[2.5]octane-1-carboxamide;
(1R)—N-[(1S)-2-amino-1-methyl-2-oxoethyl]spiro[2.5]octane-1-carboxamide;
(1S)-spiro[2.5]octane-1-carboxamide;
(1R)-spiro[2.5]octane-1-carboxamide;
2-methyl spiro[2.5]octane-1-carboxamide;
N-(2-amino-2-oxoethyl)-2-methylspiro[2.5]octane-1-carboxamide;
5,7-dimethylspiro[2.5]octane-1-carboxamide;
N-(2-amino-2-oxoethyl)-5,7-dimethylspiro[2.5]octane-1-carboxamide;
6-tert-butylspiro[2.5]octane-1-carboxamide;
N-(2-amino-2-oxoethyl)-6-tert-butylspiro[2.5]octane-1-carboxamide;
(4S,7R)-4-isopropyl-7-methylspiro[2.5]octane-1-carboxamide;
(4S,7R)—N-(2-amino-2-oxoethyl)-4-isopropyl-7-methylspiro[2.5]octane-1-carboxamide;
N-(3-amino-3-oxopropyl)spiro[2.5]octane-1-carboxamide;
5,5,7,7-tetramethylspiro[2.5]octane-1-carboxamide; or
N-(2-amino-2-oxoethyl)-5,5,7,7-tetramethylspiro[2.5]octane-1-carboxamide.

8. The method according to claim 6 wherein the compound of formula (I) is (1S)—N-(2-amino-2-oxoethyl)spiro[2.5]octane-1-carboxamide.
9. The method according to claim 6 wherein the compound of formula (I) is (1R)—N-(2-amino-2-oxoethyl)spiro[2.5]octane-1-carboxamide.
10. The method according to claim 1 wherein
$R_1$ is $NR_3R_4$;
$R_4$ is carboxyalkyl or hydroxyalkyl; and
$R_3$ is hydrogen.
11. The method according to claim 10 wherein the compound of formula (I) is
[(spiro[2.5]oct-1-ylcarbonyl)amino]acetic acid;
{[(1S)-spiro[2.5]oct-1-ylcarbonyl]amino}acetic acid;
{[(1R)-spiro[2.5]oct-1-ylcarbonyl]amino}acetic acid;
(1R)—N-[(2R)-2-hydroxypropyl]spiro[2.5]octane-1-carboxamide;
(1R)—N-[(2S)-2-hydroxypropyl]spiro[2.5]octane-1-carboxamide;
(1S)—N-[(2R)-2-hydroxypropyl]spiro[2.5]octane-1-carboxamide; or
(1S)—N-[(2S)-2-hydroxypropyl]spiro[2.5]octane-1-carboxamide.

* * * * *